US006783546B2

(12) United States Patent
Zucherman et al.

(10) Patent No.: US 6,783,546 B2
(45) Date of Patent: Aug. 31, 2004

(54) IMPLANTABLE PROSTHETIC OR TISSUE EXPANDING DEVICE

(75) Inventors: James F. Zucherman, San Francisco, CA (US); Ken Y. Hsu, S.F., CA (US); Scott Yerby, Montara, CA (US); Robert A. Smith, Jackson, MS (US)

(73) Assignee: Keraplast Technologies, Ltd., San Antonio, TX (US)

( * ) Notice: Subject to any disclaimer, the term of this patent is extended or adjusted under 35 U.S.C. 154(b) by 0 days.

(21) Appl. No.: 09/815,387

(22) Filed: Mar. 22, 2001

(65) Prior Publication Data

US 2002/0029083 A1 Mar. 7, 2002

Related U.S. Application Data

(63) Continuation-in-part of application No. 09/394,783, filed on Sep. 13, 1999, now Pat. No. 6,371,984.

(51) Int. Cl.$^7$ .................................................. A61F 2/44
(52) U.S. Cl. ................... 623/17.16; 623/17.12
(58) Field of Search ............................ 623/16.11–17.16

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 1,214,299 A | 1/1917 | Grosvenor et al. | |
| 2,434,688 A | 1/1948 | Evans | 18/47.5 |
| 2,445,028 A | 7/1948 | Jones | 106/155 |
| 2,517,572 A | 8/1950 | Jones et al. | 106/155 |
| 2,814,851 A | 12/1957 | Hervey | 28/82 |

(List continued on next page.)

FOREIGN PATENT DOCUMENTS

| | | |
|---|---|---|
| CN | 1056986 A | 12/1991 |
| DE | 3922203 C1 | 10/1990 |
| DE | 4222763 A1 | 1/1994 |
| EP | 0454600 A | 10/1991 |
| EP | 0 454 600 A1 | 10/1991 |

(List continued on next page.)

OTHER PUBLICATIONS

Southwest Research Institute Annual Report, 17–18, 21, 1997.

Technology Today, Fall 16(3):9, 1995.

(List continued on next page.)

*Primary Examiner*—Corrine McDermott
*Assistant Examiner*—Thomas C. Barrett
(74) *Attorney, Agent, or Firm*—Vinson & Elkins L.L.P.

(57) ABSTRACT

A keratin hydrogel-filled implantable prosthetic device. One device is a breast implant for augmenting or reconstructing a human breast including an envelope containing a keratin hydrogel. Another device is an implant for the intervertebral disc space. One keratin hydrogel is formed from a solid precursor which forms a keratin hydrogel upon addition of water. One source of keratin is human hair. In one method, an envelope suitable for implantation and a solid keratin hydrogel precursor are provided. The solid can be in fibrous or powder form. The solid precursor can be inserted into the envelope interior. A small incision near the breast can be made and the envelope inserted into the incision. After insertion, water can be injected into the envelope interior, preferably through the incision and through a self-sealing port in the envelope. In one method, the implant is provided as a kit, with the envelope and keratin hydrogel provided. The hydrogel can be injected into the envelope either before or after insertion into the breast area. One kit has a powdered, keratin hydrogel precursor disposed within the envelope interior, awaiting the addition of water, preferably after insertion of the implant into the body. In another method, the implant can include an envelope with a hydrogel or hydrogel precursor already placed in the envelope.

20 Claims, 5 Drawing Sheets

U.S. PATENT DOCUMENTS

| | | | |
|---|---|---|---|
| 3,033,755 A | 5/1962 | Jacobi et al. | 167/90 |
| 3,642,498 A | 2/1972 | Anker | 99/166 |
| 3,655,416 A | 4/1972 | Vinson et al. | 106/155 |
| 3,867,728 A | 2/1975 | Stubstad et al. | 3/1 |
| 3,875,595 A | 4/1975 | Froning | 3/1 |
| 3,987,497 A | 10/1976 | Stoy et al. | 3/1 |
| 4,021,382 A | 5/1977 | Stoy et al. | 260/2.5 M |
| 4,026,296 A | 5/1977 | Stoy et al. | 128/349 B |
| 4,107,121 A | 8/1978 | Stoy | 260/29.6 AB |
| 4,123,406 A | 10/1978 | Stoy et al. | 260/29.6 AN |
| 4,135,942 A | 1/1979 | Kikkawa | 106/155 |
| 4,172,823 A | 10/1979 | Stoy et al. | 260/29.6 AN |
| 4,178,361 A | 12/1979 | Cohen et al. | 424/22 |
| 4,183,884 A | 1/1980 | Wichterle et al. | 264/41 |
| 4,228,056 A | 10/1980 | Stoy | 260/29.6 AN |
| 4,309,777 A | 1/1982 | Patil | 3/1.91 |
| 4,349,921 A | 9/1982 | Kuntz | 3/1 |
| 4,357,274 A | 11/1982 | Werner | 260/123.7 |
| 4,369,037 A | 1/1983 | Matsunaga et al. | 8/127.51 |
| 4,423,032 A | 12/1983 | Abe et al. | 424/70 |
| 4,439,417 A | 3/1984 | Matsunaga et al. | 424/70 |
| 4,495,173 A | 1/1985 | Matsunaga et al. | 424/70 |
| 4,570,629 A | 2/1986 | Widra | 128/156 |
| 4,685,447 A | 8/1987 | Iversen et al. | 128/1 R |
| 4,714,469 A | 12/1987 | Kenna | 623/17 |
| 4,751,074 A | 6/1988 | Matsunaga et al. | 424/70 |
| 4,766,005 A | 8/1988 | Montgomery et al. | 427/4 |
| 4,772,287 A | 9/1988 | Ray et al. | 623/17 |
| 4,837,379 A | 6/1989 | Weinberg | 424/101 |
| 4,839,168 A | 6/1989 | Abe et al. | 424/74 |
| 4,895,722 A | 1/1990 | Abe et al. | 424/71 |
| 4,904,260 A | 2/1990 | Ray et al. | 623/17 |
| 4,904,261 A | 2/1990 | Dove et al. | 623/17 |
| 4,911,718 A | 3/1990 | Lee et al. | 623/17 |
| 4,932,969 A | 6/1990 | Frey et al. | 623/17 |
| 4,936,848 A | 6/1990 | Bagby | 623/17 |
| 4,946,378 A | 8/1990 | Hirayama et al. | 623/17 |
| 4,959,213 A | 9/1990 | Brod et al. | 514/21 |
| 4,969,888 A | 11/1990 | Scholten et al. | 606/94 |
| 5,035,716 A | 7/1991 | Downey | 623/17 |
| 5,047,055 A | 9/1991 | Bao et al. | 623/17 |
| 5,047,249 A | 9/1991 | Rothman et al. | 424/543 |
| 5,059,193 A | 10/1991 | Kuslich | 606/61 |
| 5,108,438 A * | 4/1992 | Stone | 623/17.16 |
| 5,123,926 A | 6/1992 | Pisharodi | 623/17 |
| 5,134,031 A | 7/1992 | Kagechi et al. | 428/373 |
| 5,192,326 A | 3/1993 | Bao et al. | 623/17 |
| 5,258,043 A | 11/1993 | Stone | 623/66 |
| 5,276,138 A | 1/1994 | Yamada et al. | 530/357 |
| 5,292,362 A | 3/1994 | Bass et al. | 106/124 |
| 5,304,378 A | 4/1994 | Koga et al. | 424/445 |
| 5,306,309 A | 4/1994 | Wagner et al. | 623/17 |
| 5,320,796 A | 6/1994 | Harashima et al. | 264/349 |
| 5,324,775 A | 6/1994 | Rhee et al. | 525/54.2 |
| 5,358,935 A | 10/1994 | Smith et al. | 514/21 |
| 5,390,683 A | 2/1995 | Pisharodi | 128/898 |
| 5,443,514 A | 8/1995 | Steffee | 623/17 |
| 5,458,643 A | 10/1995 | Oka et al. | 623/18 |
| 5,474,770 A | 12/1995 | Broly et al. | 424/94.64 |
| 5,480,430 A | 1/1996 | Carlisle et al. | 623/8 |
| 5,505,732 A | 4/1996 | Michelson | 606/61 |
| 5,514,180 A | 5/1996 | Heggeness et al. | 623/17 |
| 5,522,898 A | 6/1996 | Bao | 623/17 |
| 5,534,028 A | 7/1996 | Bao et al. | 623/17 |
| 5,534,029 A | 7/1996 | Shima | 623/17 |
| 5,549,672 A | 8/1996 | Maddock et al. | 623/8 |
| 5,549,679 A | 8/1996 | Kuslich | 623/17 |
| 5,552,452 A | 9/1996 | Khadem et al. | 522/63 |
| 5,561,107 A | 10/1996 | Jaynes et al. | 514/12 |
| 5,562,736 A | 10/1996 | Ray et al. | 623/17 |
| 5,589,451 A | 12/1996 | Wilson | 512/2 |
| 5,632,774 A | 5/1997 | Babian | 623/8 |
| 5,634,945 A | 6/1997 | Pernia et al. | 623/11 |
| 5,645,597 A | 7/1997 | Krapiva | 623/17 |
| 5,653,984 A | 8/1997 | Fodor et al. | 424/195.1 |
| 5,660,857 A | 8/1997 | Haynes et al. | 424/450 |
| 5,674,295 A | 10/1997 | Ray et al. | 623/17 |
| 5,676,702 A | 10/1997 | Ratron | 623/17 |
| 5,679,819 A | 10/1997 | Jones et al. | 556/418 |
| 5,694,946 A | 12/1997 | Tenerz et al. | 128/748 |
| 5,702,455 A | 12/1997 | Saggar | 623/17 |
| 5,703,047 A | 12/1997 | Wilson | 514/12 |
| 5,705,780 A | 1/1998 | Bao | 204/157.15 |
| 5,707,805 A | 1/1998 | Rubin et al. | 435/6 |
| 5,712,252 A | 1/1998 | Smith | 514/21 |
| 5,716,404 A | 2/1998 | Vacanti et al. | 623/8 |
| 5,716,415 A | 2/1998 | Steffee | 623/17 |
| 5,723,331 A | 3/1998 | Tubo et al. | 435/366 |
| 5,725,582 A | 3/1998 | Bevan et al. | 623/17 |
| 5,728,405 A | 3/1998 | McDonnell | 424/682 |
| 5,755,814 A | 5/1998 | Berg et al. | 623/66 |
| 5,763,583 A | 6/1998 | Arai et al. | 530/353 |
| 5,766,252 A | 6/1998 | Henry et al. | 623/17 |
| 5,782,831 A | 7/1998 | Sherman et al. | 606/61 |
| 5,785,964 A | 7/1998 | Naughton et al. | 424/93.21 |
| 5,786,217 A | 7/1998 | Tubo et al. | 435/402 |
| 5,791,352 A | 8/1998 | Reich et al. | 128/898 |
| 5,792,090 A | 8/1998 | Ladin | 602/48 |
| 5,800,549 A | 9/1998 | Bao et al. | 623/17 |
| 5,814,605 A | 9/1998 | Pierce et al. | 514/12 |
| 5,824,093 A | 10/1998 | Ray et al. | 623/17 |
| 5,824,113 A | 10/1998 | Hogo | 8/128.3 |
| 5,824,331 A | 10/1998 | Usala | 424/424 |
| 5,827,328 A | 10/1998 | Buttermann | 623/17 |
| 5,842,477 A | 12/1998 | Naughton et al. | 128/898 |
| 5,854,207 A | 12/1998 | Lee et al. | 514/2 |
| 5,865,846 A | 2/1999 | Bryan et al. | 623/17 |
| 5,874,500 A * | 2/1999 | Rhee et al. | 525/54.1 |
| 5,888,224 A | 3/1999 | Beckers et al. | 623/17 |
| 5,914,265 A | 6/1999 | Roop et al. | 435/320.1 |
| 5,916,565 A | 6/1999 | Rose et al. | 424/195.1 |
| 5,916,870 A | 6/1999 | Lee et al. | 514/2 |
| 5,932,552 A | 8/1999 | Blanchard et al. | 514/21 |
| 5,948,428 A | 9/1999 | Lee et al. | 424/426 |
| 5,948,432 A | 9/1999 | Timmons et al. | 424/443 |
| 5,955,083 A | 9/1999 | Bonte et al. | 424/195.1 |
| 5,972,031 A | 10/1999 | Biedermann et al. | 623/17 |
| 5,976,186 A | 11/1999 | Bao et al. | 623/17 |
| 6,004,323 A | 12/1999 | Park et al. | 606/61 |
| 6,008,013 A | 12/1999 | Reynolds | 435/69.1 |
| 6,022,376 A | 2/2000 | Assell et al. | 623/17 |
| 6,063,061 A | 5/2000 | Wallace et al. | 604/181 |
| 6,063,378 A | 5/2000 | Nohara et al. | 424/94.61 |
| 6,077,987 A | 6/2000 | Breitbart et al. | 623/11 |
| 6,093,205 A | 7/2000 | McLeod et al. | 623/17 |
| 6,105,581 A | 8/2000 | Eggers et al. | 128/898 |
| 6,110,208 A | 8/2000 | Soranzo et al. | 623/15 |
| 6,110,210 A | 8/2000 | Norton et al. | 623/17.16 |
| 6,110,487 A | 8/2000 | Timmons et al. | 424/443 |
| 6,110,891 A | 8/2000 | Pusztai et al. | 514/8 |
| 6,113,639 A | 9/2000 | Ray et al. | 623/11 |
| 6,124,265 A | 9/2000 | Timmons et al. | 514/21 |
| 6,124,273 A | 9/2000 | Drohan et al. | 514/55 |
| 6,224,630 B1 * | 5/2001 | Bao et al. | 623/17.16 |
| 6,274,163 B1 | 8/2001 | Blanchard et al. | 424/443 |

FOREIGN PATENT DOCUMENTS

| | | |
|---|---|---|
| EP | 0468797 B1 | 12/1995 |
| GB | 531446 | 1/1941 |
| JP | S55-187190 | 12/1980 |
| JP | 56129035 | 10/1981 |

| | | |
|---|---|---|
| JP | SHO 54-124043 | 2/1982 |
| JP | SHO59-155248 | 9/1984 |
| JP | SHO 60-220068 | 11/1985 |
| JP | 1988-202582 | 8/1988 |
| JP | 03011099 A | 1/1991 |
| JP | 04091138 A | 3/1992 |
| JP | 04091138 A2 | 3/1992 |
| JP | 1992-174659 | 5/1992 |
| JP | HEI 4-189833 | 7/1992 |
| JP | 5285374 | 11/1993 |
| JP | 5285375 | 11/1993 |
| JP | 1993285374 A | 11/1993 |
| JP | 1993285375 A | 11/1993 |
| JP | 6116300 | 4/1994 |
| JP | 1994100600 A | 4/1994 |
| JP | 1994116300 A | 4/1994 |
| JP | HEI 6-293631 | 10/1994 |
| JP | 06336499 A | 12/1994 |
| JP | 6336499 | 12/1994 |
| JP | 1998291999 A | 11/1998 |
| JP | 1998337466 A | 12/1998 |
| JP | 2001087754 | 4/2001 |
| WO | WO 91/02538 | 3/1991 |
| WO | WO 98/08550 | 3/1998 |
| WO | WO 99/04720 * | 2/1999 ........... A61B/19/00 |
| WO | WO 99/26595 * | 6/1999 ........... A61K/7/06 |
| WO | WO 03/011894 A1 | 2/2003 |
| WO | WO 03/018673 A1 | 3/2003 |

OTHER PUBLICATIONS

Wake, et al., "Dynamics of fibrovascular tissue ingrowth in hydrogel foams," Cell Transplantation 4(3), 275–79, 1995.

Plant, et al., "Axonal growth within poly (2–hydroxyethyl methacrylate) sponges infiltrated with schwann cells and implanted into the lesioned rat optic tract," Brain Research, 671,119–30, 1995.

Rhodes, et al., "Characteristics of the alpha–keratose fraction of hair inducing ascosporogensis in nannizzia grubyia," Mycopathologia et Mycologia Applicata, 33, 345–48, 1967.

Chargaff, et al., "Techniques for the demonstration by chromatography of nitrogenous lipide constituents, sulfur–containing amino acids, and reducing sugars," J. Biol. Chem., 175(1):67–71, 1948.

Yamauchi, et al., "Cultivation of fibroblast cells on keratin–coated substrates," Polymers for Tissue Engineering, 329–40, 1998.

Thomas et al., "Isolation of microfibrillar proteins of wool in disulfide form," Melliand Textiberichte, 65(3):20809, 1984.

van de Löcht, "Reconstitution of microfibrils from wool and filaments from epidermis proteins," Melliand Textiberichte, 10:780–6, 1987.

Yoshioka et al., "Cosmetic base," unexamined Japanese patent application No. 3–223207, Oct. 2, 1991.

Yoshioka et al., "Water–soluble hair dressing agent," unexamined Japanese patent application No. 8–157342, Jun. 18, 1996.

Hyuku et al., "Novel amino acid silicone polymer, production thereof, cosmetic particles surface treated with the polymer, and cosmetic containing said particles," unexamined Japanese patent application No. 2001–114647, Apr. 24, 2001.

Ito et al., "Biocompatibility of denatured wool keratin," 39:4, 249–256, Apr. 1982.

Yamauchi, "The development of keratin: characteristics of polymer films," Fragrance J, 21(5), 62–7, 1993.

Sauk et al, "Reconstitution of cytokeratin filaments in vitro: further evidence for the role of nonhelical peptides in filament assembly," The Journal of Cell Biology, 99, 1590–1597, Nov. 1984.

Weber et al., "The structural relation between intermediate filament proteins in living cells and the α–keratins of sheep wool," The EMBO Journal, 1:10, 1155–1160, 1982.

Hanukoglu et al., "The cDNA sequence of a human epidermal keratin: divergence of sequence but conservation of structure among intermediate filament proteins," Cell, 31, 243–252, Nov. 1982.

Fraser et al., "Intermediate filaments in α–keratins," Proc. Natl. Acad. Sci. USA, 83, 1179–1183, Mar. 1986.

Jones, "Studies on microfibrils from α–keratin," Biochimica et Biophysica Acta, 446, 515–524, Received Apr. 5th, 1976.

Zackroff, et al., "In vitro assembly of intermediate filaments from baby hamster kidney (BHK–21) cells," Proc. Natl. Acad. Sci. USA, 76:12, 6226–6230, Dec. 1979.

Mack, et al., "Solid–state NMR studies of the dynamics and structure of mouse keratin intermediate filaments," Biochemistry, 27, 5418–5426, 1988.

Skerrow, et al., "Epidermal α–keratin is neutral–buffer–soluble and forms intermediate filaments under physiological conditions in vitro," Biochimica et Biophysica Acta, 915, 125–131, 1987.

Kvedar, et al., "Cytokeratins of the bovine hoof: classification and studies on expression," Biochimica et Biophysica Acta, 884, 462–473, 1986.

Moll, et al., "The catalog of human cytokeratins: patterns of expression in normal epithelia, tumors and cultured cells," Cell, 31, 11–24, Nov. 1982.

Iwatsuki, et al., "Comparative studies on naturally occurring antikeratin antibodies in human sera," The Journal of Investigative Dermatology, 87:2, 179–184, Aug. 1986.

Lambré, et al., "An enzyme immunoassay for auto–antibodies to keratin in normal human serum and in pleural fluids from patients with various malignant or non–malignant lung diseases," J. Clin. Lab. Immunol., 20, 171–176, 1986.

Stokes, et al., "Passage of water and electrolytes through natural and artificial keratin membranes," Desalination, 42, 321–328, 1982.

Dedeurwaerder, et al., "Selective extraction of a protein fraction from wool keratin," Nature, 265, 48–49 and 274–276, Jan. 20, 1977.

Brunner, et al., "Fractionation of tyrosine–rich proteins from oxidized wool by ion–exchange chromatography and preparative electrophoresis," Eur. J. Biochem., 32, 350–355, 1973.

Mies, et al., "Chromatographic and electrophoretic investigations of the properties of unprotected low–sulphur wool kerateins," Journal of Chromatography, 405, 365–370, 1987.

Katsuumi, et al., "Two–dimensional electrophoresis analysis of human hair keratins, especially hair matrix proteins," Arch. Dermatol Res., 281, 495–501, 1989.

Horn, et al., "Relative molecular masses of reduced wool keratin polypeptides," Biochem Soc Trans, 14, 333–334, 1986.

Harrap, et al., "Species differences in the proteins of feathers," Comp. Biochem. Physiol., 20, 449–460, 1967.

Harrap, et al., "Soluble derivatives of feather keratin," Biochem. J., 92, 8–18, 1964.

Yoshimizu, et al., "$^{13}$C CP/MAS NMR study of the conformation of stretched or heated low–sulfur keratin protein films," *Macromolecules*, 24, 862–866, 1991.

Schaller, et al., "Membranes prepared from keratin–polyacrylonitrile graft copolymers," *Journal of Applied Polymer Science*, 25, 783–794, 1980.

Weiss, et al., "The use of monoclonal antibody to keratin in human epidermal disease: alterations in immunohistochemical staining pattern," *The Journal of Investigative Dermatology*, 81, 224–230, 1983.

Starger, et al., "Biochemical and immunological analysis of rapidly purified 10–nm filaments from baby hamster kidney (BHK–21) cells," *J. Cell Biology*, 78, 93–109, 1978.

Noishiki, et al., "Application of denatured wool keratin derivatives to an antithrombogenic biomaterial—vascular graft coated with a heparinized keratin derivative—," *Inst. Thermal Spring Res. Okayama Univ.*, 39:4, 221–227, 1982.

Dale, "Keratin and other coatings for pills," *Pharm. J.*, 129, 494–495, 1932, Abstract.

Schrooyen, et al., "Biodegradable films from selectively modified feather keratin dispersions," *Polymer Preprints (American Chemical Society, Division of Polymer Chemistry)*, 39(2), 160, 1998, Abstract.

Schrooyen, et al., "Polymer films from chicken feather keratin," Book of Abstracts, 216th ACS National Meeting, Boston, Aug. 23–27, 1998, Abstract.

Kikkawa, et al., "Solubilization of keratin. 6. Solubilization of feather keratin by oxidation with performic acid," *Hikaku Kagaku*, 20(3), 151–162, 1974, Abstract.

Matsunaga, et al., "Studies on the chemical property of human hair keratin. Part 1. Fractionation and amino acid Composition of human hair keratin solubilized by performic acid oxidation," *Hikaku Kagaku*, 27(1), 21–29, 1981, Abstract.

Noishiki, et al., "Applications of denatured wool keratin derivatives to an antithrombogenic biomaterial. Vascular graft coated with a heparinized keratin derivative," *Kobunshi Ronbunshu*, 39(4), 221–227, 1982, Abstract.

Ito, et al., "Biocompatibility of denatured keratins from wool," *Kobunshi Ronbunshu*, 39(4), 249–256, 1982, Abstract.

Gillespie, et al., "Amino acid composition of a sulphur–rich protein from wool," *Biochimica et Biopysica Acta*, 39, 538–539, 1960.

Gough, et al., "Amino acid sequences of α–helical segments from S–carboxymethylkerateine–A. Complete sequence of a type–I segment," *Biochem. J.*, 173, 373–385, 1978.

Elleman, et al., "Amino acid sequences of α–helical segments from S–carboxymethylkerateine–A. Statistical analysis," *Biochem. J.*, 173, 387–391, 1978.

Hogg, et al., "Amino acid sequences of α–helical segments from S–carboxymethylkerateine–A. Tryptic and chymotryptic peptides from a type–II segment," *Biochem. J.*, 173, 353–363, 1978.

Earland, et al., "Studies on the structure of keratin. II. The amino acid content of fractions isolated from oxidized wool," *Biochimica et Biophysica Acta*, 22, 405–411, 1956.

Crewther, et al., "Amino acid sequences of α–helical segments from S–carboxymethylkerateine–A. Complete sequence of a type–II segement," *Biochem. J.*, 173, 365–371, 1978.

Fraser, et al., "Microscopic observations of the alkaline–thioglycollate extraction of wool," *Biochimica et Biophysica Acta*, 22, 484–485, 1953.

Gillespie, et al., "Preparation of an electrophoretically homogeneous keratin derivative from wool," *Biochimica et Biophysica Acta*, 12, 481–483, 1953.

Blagrove, et al., "The electrophoresis of the high–tyrosine proteins of keratins on cellulose acetate strips," *Comp. Biochem. Physiol.*, 50B, 571–572, 1975.

Frenkel, et al., "The isolation and properties of a tyrosine–rich protein from wool: component 0.62," *Eur. J. Biochem.*, 34, 112–119, 1973.

Marshall, et al., "Successful isoelectric focusing of wool low–sulphur proteins," *Journal of Chromatography*, 172, 351–356, 1979.

Marshall, "Characterization of the proteins of human hair and nail by electrophoresis," *The Journal of Investigative Dermatology*, 80:6, 519–524, 1983.

Lindley, et al., "Occurrence of the cys–cys sequence in keratins," *J. Mol. Biol.*, 30, 63–67, 1967.

Marshall, "Genetic variation in the proteins of human nail," *The Journal of Investigative Dermatology*, 75:3, 264–269, 1980.

Goddard, et al., "A study on keratin," *J. Bio. Chem.*, 106, 605–614, 1934.

Dowling, et al., "Isolation of components from the low–sulphur proteins of wool by fractional precipitation," *Preparative Biochemistry*, 4(3), 203–226, 1974.

Crewther, et al., "Reduction of S–carboxymethylcysteine and methionine with sodium in liquid ammonia," *Biochimica et Biophysica Acta*, 194, 606–609, 1969.

Gillespie, "The isolation from wool of a readily extractable protein of low sulphur content," *Biochimica et Biophysica Acta*, 27, 225–226, 1958.

Lindley, et al., "The reactivity of the disulphide bonds of wool," *Biochem. J.*, 139, 515–523, 1974.

Mitsui, et al., "Genes for a range of growth factors and cyclin–dependent kinase inhibitors are expressed by isolated human hair follicles," *British Journal of Dermatology*, 137(5), 693–698, 1997, Abstract.

Schörnig, et al., "Synthesis of nerve growth factor mRNA in cultures of developing mouse whisker pad, a peripheral target tissue of sensory trigeminal neurons," *The Journal of Cell Biology*, 120:6, 1471–1479, 1993.

Filshie, et al., "The fine structure of α–keratin," *J. Mol. Biol.*, 3, 784–786, 1961.

Filshie, et al., "An electron microscope study of the fine structure of feather keratin," *The Journal of Cell Biology*, 13, 1–12, 1962.

Crewther, et al., "Low–sulfur proteins from α–keratins. Interrelationships between their amino acid compositions, α–helix contents, and the supercontraction of the parent keratin," *Biopolymers*, 4, 905–916, 1966.

Bhatnagar, et al., "The conformation of the high–sulphur proteins of wool. I. The preparation and properties of a water–soluble metakeratin," *Int. J. Protein Research I*, 199–212, 1969.

Crewther, et al., "The preparation and properties of a helix–rich fraction obtained by partial proteolysis of low sulfur S–carboxymethylkerateine from wool," *The Journal of Biological Chemistry*, 242:19, 4310–4319, 1967.

Parry, et al., "Structure of α–keratin: structural implication of the amino acid sequences of the type I and type II chain segments," *J. Mol. Biol.*, 113, 449–454, 1977.

Suzuki, et al, "X-ray diffraction and infrared studies of an α–helical fragment from α–keratin," *J. Mol. Biol.*, 73, 275–278, 1973.

Bhatnagar, et al., "The conformation of the high–sulphur proteins of wool. II. Difference spectra of kerateine–B," *Int. J. Protein Research I*, 213–219, 1969.

Steinert, et al., "In vitro studies on the synthesis of guinea pig hair keratin proteins," *Biochimica et Biophysica Acta*, 312, 403–412, 1973.

Rogers, "Some observations on the proteins of the inner root sheath cells of hair follicles," *Biochimica et Biophysics Acta*, 29, 33–42, 1958.

Tachibana, et al., "Fabrication of wool keratin sponge scaffolds for long–term cell cultivation," *Journal of Biotechnology*, 93, 165–170, 2002.

Gillespie, "Proteins rich in glycine and tyrosine from keratins," *Comp. Biochem. Physiol.*, 41B, 723–734, 1972.

Fraser, et al., "Tyrosine–rich proteins in keratins," *Comp. Biochem. Physiol.*, 44B, 943–947, 1973.

Bendit, et al., "Communications ot the Editor. The probable role and location of high–glycine–tyrosine proteins in the structure of keratins," *Biopolymers*, 17, 2743–2745, 1978.

Lindley, et al., "The preparation and properties of a group of proteins from the high–sulphur fraction of wool," *Biochem. J.*, 128, 859–867, 1972.

Gillespie, et al., "Evidence of homology in a high–sulphur protein fraction (SCMK–B2) of wool and hair α–keratins," *Biochem. J.*, 110, 193–198, 1968.

Gillespie, et al., "A comparative study of high–sulphur proteins from α–keratins," *Comp. Biochem. Physiol.*, 15, 175–185, 1965.

Wormell, "Regenerated protein fibres from wool and casein," *The Journal of the Textile Institute*, 18, T219–T224, 1948.

Harding, et al., "Formation of the $_e$–(γ–glutamyl) lysine cross–link in hair proteins. Investigation of transamidases in hair follicles," *Biochemistry*, 11:15, 2858–2863, 1972.

Powell, et al., "Control of feather keratin synthesis by the availability of keratin mRNA," *Biochemical and Biophysical Research Communications*, 68:4, 1263–1271, 1976.

Strüssmann, et al., "Specific radiolabelling of kertin proteins by amidination," *Journal of Chromatography*, 268, 306–310, 1983.

Lindley, et al., "Disulphide interchange reactions involving cyclocystine and their relevance to problems of α–keratin structure," *Biochem. J.*, 108, 701–703, 1968.

Damoglou, et al., "The hydrolysis by thermolysin of dipeptide derivatives that contain substituted cysteine," *Biochem. J.*, 123, 379–384, 1971.

Lennox, et al., "Photochemical degradation of keratins," *Photochemistry and Photobiology*, 9, 359–367, 1969.

Crewther, et al., "Preliminary Notes. The relation between the disulphide content of wool and the two–stage supercontraction of wool fibres in solutions of LiBr," *Biochimica et Biophysica Acta*, 46, 605–606, 1961.

Gillespie, et al., "A comparison of the proteins of normal and trichothiodystrophic human hair," *The Journal of Investigative Dermatology*, 80, 195–202, 1983.

Gillespie, et al., "Changes in the proteins of wool following treatment of sheep with epidermal growth factor," *The Journal of Investigative Dermatology*, 79:3, 197–200, 1982.

Gillespie, et al., "Changes in the matrix proteins of wool and mouse hair following the administration of depilatory compounds," *Aust. J. Biol. Sci.*, 33, 125–136, 1980.

Darskus, et al., "Breed and species differences in the hair proteins of four genera of caprini," *Aust. J. Biol. Sci.*, 24, 515–524, 1971.

Kemp, et al., "Differentiation of avian keratinocytes. Characterization and relationships of the keratin proteins of adult and embryonic feathers and scales," *Biochemistry*, 11:6, 969–975, 1972.

Gillespie, et al., "The diversity of keratins," *Comp. Biochem. Physiol.*, 47B, 339–346, 1974.

Fraser, et al., "Wool stucture and biosynthesis," *Nature*, 261, 650–654, 1976.

Stenn, et al., editors, "The molecular and structural biology of hair," *Annals of the New York Academy of Sciences*, vol. 642, Title Page—31, 1991.

Reis, et al., "The utilization of abomasal supplements of proteins and amino acids by sheep with special reference to wool growth," *Aust. J. Biol., Sci.*, 25, 1057–1071, 1972.

Broad, et al., "The influence of sulphur–containing amino acids on the biosynthesis of high–sulphur wool proteins," *Aust. J. Biol. Sci.*, 23, 149–164, 1970.

Reis, "The influence of dietary protein and methionine on the sulphur content and growth rate of wool in milk–fed lambs," *Aust. J. Biol. Sci.*, 23, 193–200, 1970.

Downes, et al., "Metabolic fate of parenterally administered sulphur–containing amino acids in sheep and effects on growth and composition of wool," *Aust. J. Biol. Sci.*, 23, 1077–1088, 1970.

Reis, "The growth and composition of wool. IV. The differential response of growth and of sulphur content of wool to the level of sulphur–containing amino acids given per abomasum," *Aust. J. Biol. Sci.*, 20, 809–825, 1967.

Reis, et al., "Effects of phenylalanine and analogues of methionine and phenylalanine on the composition of wool and mouse hair," *Aust. J. Biol. Sci.*, 38:2, 151–163.

Frenkel, et al., "Studies on the inhibition of synthesis of the tyrosine–rich proteins of wool," *Aust. J. Biol. Sci.*, 28, 331–338, 1975.

Frenkel, et al., "Factors influencing the biosynthesis of the tyrosine–rich proteins of wool," *Aust. J. Biol. Sci.*, 27, 31–38, 1974.

Reis, "The growth and composition of wool. III. Variations in the sulphur content of wool," *Aust. J. Biol. Sci.*, 18, 671–687, 1965.

Reis, et al., "The influence of abomasal and intravenous supplements of sulphur–containing amino acids on wool growth rate," *Aust. J. Biol. Sci.*, 26, 249–258, 1973.

Gillespie, et al., "A further study on the dietary–regulated biosynthesis of high–sulphur wool proteins," *Biochem. J.*, 112, 41–49, 1969.

Gillespie, et al., "The dietary–regulated biosynthesis of high–sulphur wool proteins," *Biochem. J.*, 98, 669–677, 1966.

Powell, et al., "Characterization of a gene encoding a cysteine–rich keratin associated protein synthesized late in rabbit hair follicle differentiation," *Differentiation*, 58, 227–232, 1995.

Powell, et al., "Cyclic hair–loss and regrowth in transgenic mice overexpressing an intermediate filament gene," *The EBMO Journal*, 9:5, 1485–1493, 1990.

Raphael, et al., "Protein and amino acid composition of hair from mice carrying the naked (N) gene," *Genet. Res. Camb.*, 44:1, 29–38, 1984.

Frenkel, et al., "The keratin BIIIB gene family: isolation of cDNA clones and structure of a gene and a related pseudogene," *Genomics*, 4, 182–191, 1989.

Dowling, et al., "The primary structure of component 8c–1, a subunit protein of intermediate filaments in wool keratin," *Biochem. J.*, 236, 695–703, 1986.

Dowling, et al., "Secondary structure of component 8c–1 of α–keratin," *Biochem. J.*, 236, 705–712, 1986.

Kuczek, et al., "Sheep wool (glycine + tyrosine)–rich keratin genes," *Eur. J. Biochem.*, 166, 79–85, 1987.

Inagaki, et al., "Functionality of lamb wool keratin derivatives and a few characteristics of polymer materials for medical applications," *Chemical Research Institute, Kyoto University*.

Sakabe, et al., "Differential thermal analysis of component proteins from wool," Sen–I Gakkaishi 39(12): T–517–T–522 (1982).

"Biomaterial forefront. Keratin which can be extracted by a simple chemical technique," Kogyo Zairyo (Engineering Materials), 41:15, 106–109, 1993.

Kulkarni, "Further studies on the microfibrils from wool keratin. Part I: the isolation of microfibrils," Text. Res. J., 46:11, 833–5, 1976, Abstract.

Edwards, "Chemical studies on powdered keratins," *The Journal of Biological Chemistry*, 154, 593–596, 1944.

* cited by examiner

IMPLANTABLE PROSTHETIC OR TISSUE EXPANDING DEVICE

CROSS REFERENCE TO CO-PENDING APPLICATIONS

This application is a continuation-in-part of U.S. patent application Ser. No. 09/394,783, filed Sep. 13, 1999 now U.S. Pat. 6,371,984.

FIELD OF THE INVENTION

The present invention is generally related to medical prostheses or implants for augmentation, tissue expansion or replacement of soft tissue, including breast implants and vertebral disc, nucleus and annulus replacements. In particular, the present invention is related to implants filled with a keratin hydrogel.

BACKGROUND OF THE INVENTION

Breast augmentation and reconstruction through medical procedures have been performed by physicians for decades. Early attempts using filler materials alone, without an enclosing envelope, had less than optimal long-term effects on appearance and health. The use of silicone gel-filled silicone envelopes gave improved long-term appearance but has created concerns for manufacturers, surgeons and patients due to possible leakage of the silicone gel from the envelopes into the body. These concerns had the effect of removing silicone gel-filled breast implants from some markets, such as the United States. Saline-filled breast implants have been used in place of the silicone-filled implants. The use of saline has led to fewer concerns, but saline-filled silicone implants have been reported as having a less natural shape and consistency.

Another issue in the field of breast reconstruction and in the healing of open wounds is the use of tissue expanders. Tissue expanders typically include a bladder or envelope that will hold a liquid such as saline. The expander is placed over a wound, or may be implanted under tissue, such as under the muscles below a surgically removed breast. During use in breast reconstruction, a small amount of saline is added to the envelope periodically until the desired size is reached. By adding liquid slowly over a period of weeks or months, the covering tissue is allowed to expand to accommodate its size. Tissue expanders may also be used to cover an open wound and serve as a platform for the growth of new skin over the wound. Unfortunately, in order to change the volume of the tissue expander a needle must be inserted into the envelope, thus requiring penetration of the tissue and causing pain and an increased possibility of infection.

What would be desirable is a safe, non-toxic, non-antigenic material for use in implants that has a consistency more like that of the original human soft tissue. A further advantage would be an implant that can be implanted using potentially minimally invasive surgical procedures. What would be desirable is a tissue expander that is able to absorb fluid from the patient after implantation so that the expander could reach the desired size without repeated intrusive procedures.

SUMMARY OF THE INVENTION

The present disclosure addresses the shortcomings of the prior art by providing a safer, more natural appearing implant for augmenting or reconstructing the human breast or other tissue such as intervertebral disc, nucleus, or annulus tissue, and penile, testicular, gluteal, or facial tissue. Preferred implants include an outer envelope made of silicone or a biocompatible polymer and having an interior containing a keratin hydrogel. The hydrogel can be made from a keratinous material that is obtained from a biological source, especially keratin obtained from hair, feathers, hooves, feet, beaks, skin or nails of a mammal. The keratin is preferably obtained from hair, and more preferably from human hair. Human hair is especially desirable because of its ready availability as cuttings from barber and beauty shops, because human hair is likely to have less antigenicity in a human subject, and because hair can be harvested from the intended implant recipient. In certain embodiments implants include a hydrogel formed from hydrating a keratin material prepared as described in commonly assigned U.S. patent application Ser. No. 09/394,782, incorporated herein by reference. In certain embodiments implants include a keratin hydrogel formed using an alternative method as described in U.S. Pat. Nos. 5,932,552 and 6,159,496, and in commonly assigned U.S. patent application Ser. No. 09/736,957 all incorporated herein by reference.

In more detail, a keratin hydrogel for use in the prosthetic devices described herein may be formed by adding an aqueous solvent such as water to a hydratable keratin material. This hydratable material can be made by a first process beginning with providing a keratinous material including keratin having disulfide bonds and partially oxidizing the keratin disulfide bonds, such that sulfonic acid residues are formed. The sulfonic acid containing keratin material can subsequently be placed in a solvent containing cations, preferably monovalent cations. In certain preferred embodiments, a solution containing the oxidized keratin material is neutralized, or raised to a pH that is less acidic than the oxidation solution. Without limiting the patent to a particular mechanism, in certain embodiments, and depending on the solvent used, the pH may be raised to a level above the pKa of the sulfonic acid groups to obtain sulfonic acid groups in an anionic state, or having a negative charge. It is contemplated that anionic sulfonic acid groups may more easily form ionic associations or even ionic bonds with the cations. When a substantial part of the liquid is removed from the keratin/cationic solution, a salt or solid salt including the keratin and cations may be isolated. This solid is hydratable, highly absorbent, and forms a hydrogel upon re-hydration. The solid may be used in fibrous or powdered form, and adding water to the solid forms a viscoelastic hydrogel suitable for use as a prosthetic implant filler.

A preferred source of keratinous material is human hair, although the keratin may be obtained from hair or fur of animals including any mammal, from finger or toenail material or from hooves, or from the beaks, feet or feathers of birds. Human hair is a preferred source of keratin because of its ready availability from cuttings of barber and beauty shops, because it is expected to be less prone to cause undesirable immune or allergic reactions in a human should any leakage occur, and because a keratin preparation may be made from the hair of a subject for whom the preparation will be used. This last advantage can be especially important in embodiments involving subdermal implantations.

It is well known in the art that keratins are highly sulfated, that is, the amino acid sequence of keratin contains a high proportion of cysteine residues as compared to proteins in general. These cysteines each include a sulfhydryl moiety that is able to bond with another sulfhydryl moiety from another cysteine residue to form a disulfide bond known as a cystine residue. The second cysteine may reside within the same keratin molecule, or in another keratin molecule. These disulfide bonds are responsible for much of the tertiary and/or quaternary structure of this class of proteins. A suitable oxidizing agent is able to break this disulfide bond and to oxidize one or both of the sulfide moieties so that they are no longer able to form a disulfide. Such an oxidation is a part of the process of forming the keratin products of the present disclosure. Preferred oxidizing agents include, but are not limited to peracetic acid, hydrogen peroxide, perborates, percarbonates, benzoyl peroxide, or ammonium sulfate peroxide. However, any suitable oxidizing agent known in the art can be used in the practice of the invention. After oxidation, the liquid oxidizing agent can be filtered from the oxidized keratin solid, and the solid may be washed to remove residual oxidizing agent, for example.

The resulting solid may then be suspended in a non-aqueous solvent and the pH may be adjusted upward with base-conveniently to at least neutral pH. Preferred solvents for this second solution do not include significant water as the water may hydrolyze the peptide backbone during processing. Preferred solvents would include alcohols such as methanol, ethanol, or propanol, for example, and would also include non-aqueous solvents such as acetone and tetrahydrofuran, for example. An effective solvent should be able to solvate a base and should also be able to provide a medium able to keep the keratin sufficiently open to allow ionic associations or interactions between the base cations and anionic sulfonic acid groups in the keratin. Preferred bases include, but are not limited to sodium hydroxide, potassium hydroxide and ammonium hydroxide, which, as is known in the art, would yield or produce sodium, potassium and ammonium ions, respectively, upon entering solution.

The keratin suspension may be heated, and is preferably heated to boiling for a time sufficient to swell the keratin. The keratin suspension may be stirred without heat for a longer period of time to allow a more complete association or reaction between the sulfonic acid groups and the base cations. The continued reaction time at or near room temperature, or even below room temperature while stirring is contemplated by the inventors to allow the base cations to approach and bind to the keratin anionic sites with a lower incidence of peptide backbone degradation that could occur with continued boiling. The cations for use in the present invention, therefore, must be able to interact with the anionic cysteic acid groups in the keratin material. The use of the term "cations" or "monovalent cations" in the present disclosure and claims is an indication of those cations that are able to form such an interaction. After a sufficient reaction time, the keratin solid may be removed from the suspension by filtration, for example, and dried, leaving a solid salt formed of the keratin sulfonic acid or cysteic acid groups and base cations. This solid may be shredded into a fibrous form and/or ground into a finely divided powder. This solid may be used in certain embodiments, or it may be hydrated by adding water, for example, and the hydrogel, or viscoelastic hydrogel thus formed may be used in certain embodiments.

The keratin hydrogel so formed is suitable for use as an implant filler, for example, used to fill a breast implant, or to augment soft tissue for cosmetic, reconstructive or aesthetic reasons, or it may be used in a tissue expander. In certain embodiments, a dry keratin hydrogel precursor may be placed in a semipermeable silicone shell, for example and implanted in a body cavity, wound, or scar where new tissue growth is needed. This technique is known in the art to be useful in breast reconstruction, in treatment of male pattern baldness, for treatment of wounds, birth defects, and the like. This technique can also be used to create an intervertebral disc, nucleus and/or annulus.

The present invention may be described, therefore, in certain aspects as a prosthetic device or implant, or even a tissue expander device, wherein the device includes a composition comprising a hydratable keratin solid to be used as a filler for the device, wherein the solid comprises a keratin where at least a portion of the cysteic groups of the keratin are ionically associated with, or may be ionically bound to cations. As used herein, ionically bound or ionically associated would have their ordinary meaning as is known in the art, and would include the electrostatic attraction between an anion and a cation, and would include such interactions directly, such as through formation of ionic bonds, and interactions through intermediary bipolar moieties, for example. A cysteic group would include cysteine and derivatives of cysteine including cystine and cysteic acid. As used herein, cysteic acid and sulfonic acid denote a cysteine side chain in which the terminal sulfur is bonded to three oxygen atoms to produce the sulfonic acid ion, $SO_3-$, or the acidic form, $SO_3H$. In certain embodiments, a portion of the cysteic groups are oxidized to cysteic acid groups. Cysteic acid groups may comprise a significant portion of the total cysteic groups. The extent of the oxidation may be adjusted by adjusting certain parameters of the oxidation reactions, such as temperature, concentration of oxidizing agent, and time of reaction, for example, to achieve a product with certain desired properties, such as absorbency or resiliency, for example.

In certain embodiments, therefore, the hydratable keratin solid is made by a process comprising oxidizing a portion of the disulfide groups of a keratin to obtain a keratin having oxidized cysteic groups, and contacting the keratin having oxidized cysteic groups with monovalent cations under conditions effective to form ionic associations or ionic bonds between at least a portion of the oxidized cysteic groups and the cations.

In some embodiments, the hydratable keratin solid is made by a process comprising oxidizing at least a portion of the disulfide groups of a keratin to obtain a keratin having oxidized cysteic groups, and contacting said keratin having oxidized cysteic groups with monovalent cations under conditions effective to form ionic associations or ionic bonds between a substantial portion of said oxidized cysteic groups and said cations. The oxidization may comprise placing the keratin in a solution containing a concentration of an oxidizing agent effective to oxidize a portion of the disulfide groups. The portion of oxidized disulfide groups may be a major portion of the total cysteic acid groups.

In certain embodiments of the present invention, the oxidation comprises placing the keratin in a solution containing a concentration of hydrogen peroxide, peracetic acid, perborates, percarbonates, benzoyl peroxide, or ammonium sulfate peroxide effective to oxidize a portion of the disulfide groups.

The process of the present invention may further comprise heating the keratin solid containing oxidized cysteic groups in a solvent solution containing a dissolved base. The solvent solution may comprise a solvent selected from methanol, ethanol, propanol, ether, tetrahydrofuran (THF), and acetone. In certain embodiments the process further comprises removing the solution from the heat and stirring for a time effective to form ionic bonds between the cysteic acid groups and cations produced by the base. The process may also further comprise drying the keratin solid, such as by drying a solid or solution under vacuum.

Another aspect of the present invention includes prosthetic implants that comprise a keratin hydrogel wherein the hydrogel is produced by adding water to a composition comprising a hydratable keratin solid, wherein the solid comprises a keratin where at least a portion of the cysteic acid groups of the keratin are ionically bound to cations. In some embodiments, the hydrogel is a keratin viscoelastic hydrogel produced by adding water to a composition comprising a hydratable keratin solid, wherein the solid comprises a keratin where a portion of the cysteic acid groups of the keratin are ionically bound to or associated with cations.

Another aspect of the present invention is the use in a prosthetic implant of a hydratable keratin solid made by (1) oxidizing keratin in a first solution comprising a soluble oxidizing agent, such that a portion of the disulfide bonds of the keratin are oxidized to form cysteic acid residues, to obtain an oxidized solid fraction; (2) separating the oxidized solid fraction from the first solution; (3) contacting the oxidized solid fraction with a second, basic solution comprising a monovalent cation dissolved in a solvent; (4) maintaining the second solution containing the oxidized solid fraction and the monovalent cations for a time and at a temperature effective to cause an interaction between the cysteic acid residues and the monovalent cations to obtain a salt solution of the keratin and the monovalent cation; and (5) substantially removing the solvent from the salt solution to obtain a hydratable keratin solid.

The process may also further comprise adjusting the pH of the second solution, to obtain a substantially neutral solution. In some embodiments, the keratin is obtained from hair or fur, and is preferably obtained from human hair.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent. In various embodiments, the keratin is oxidized by suspending the keratin in a solution of an oxidizing agent selected from the group consisting of hydrogen peroxide, peracetic acid, perborates, percarbonates, benzoyl peroxide, and ammonium sulfate peroxide, in a concentration of about 1, or about 2, or about 3, or about 4, or about 10, or about 15, or about 20, or about 30, or about 32, or about 35 weight/volume percent. As used herein the term weight/volume percent refers to a solution in which the concentration is determined in weight percent, that is then diluted into a particular volume, arriving at a weight/volume percent. For example, in order to arrive at the oxidant solutions described herein a "stock solution" at fairly high concentration is diluted in water. As an example, hydrogen peroxide may be purchased as a 30 weight % solution (30 grams of peroxide per 100 grams of solution). To make 1 liter of a 2% solution of this, one would dilute 66.7 mL of the 30 weight % stock solution in 933.7 mL of water. The net effect is to cut the stock solution 15-fold (from 30 down to 2%). This ratio is a weight to volume ratio, so the resulting solution is described as 2 weight/volume %.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. In other embodiments the temperature is between about 4° C. and about 90° C., or between about 20° C. and about 100° C., or between about 80° C. and about 100° C. In other embodiments, the temperature is about 4° C., or about 90° C., or about 100° C.

The present invention may also include the process wherein the keratin is oxidized by suspending said keratin in a solution of an oxidizing agent selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. for a period of between 0.5 and about 24 hours, or in a concentration of oxidizing agent of between about 1 and about 35 weight/volume percent, at a temperature between about 0° C. and about 100° C. for a period of between 1 and about 2 hours, or for between about 2 and about 4 hours, or for between about 1 and about 4 hours, or for a period of about 10 hours.

More specifically, the process of making the keratin solid may include oxidizing the keratin by suspending the keratin in a solution of between about 1 percent to about 32 percent peracetic acid at a temperature between about 0° C., and about 100° C. for between about 0.5 and about 24 hours, or by suspending the keratin in a solution of about 1 percent peracetic acid at a temperature between about 0° C. and about 100° C. for between about 0.5 and about 24 hours, or by suspending the keratin in a solution of between about 4 percent peracetic acid at a temperature of about 40° C. for 24 hours, or by suspending the keratin in a solution of about 4 percent peracetic acid at room temperature for about 24 hours, or by suspending the keratin in a solution of about 4 percent peracetic acid at about 90° C. for about 10 hours, or by suspending the keratin in a solution of about 4 percent peracetic acid at a temperature between about 20° C. and about 100° C. for between about 1 and about 4 hours, or by suspending the keratin in a solution of about 4 percent peracetic acid at a temperature between about 80° C. and about 100° C. for between about 1 and about 2 hours, or even by suspending the keratin in a solution of about 2 percent peracetic acid at a temperature between about 0° C. and about 100° C. for about 2 hours.

A second solution in the process of making the disclosed keratin compositions, wherein the second solution contains the oxidized solid fraction and monovalent cations may be heated, and may also be boiled for between about 0.5 hours and about 12 hours, for between about 0.5 hours and about 3 hours, or for about 1 hour. When said solution is boiled, the solution may be allowed to continue reacting while being stirred after removal of the heat. Alternatively, the solution may be stirred and allowed to react without the application of heat, or of boiling temperatures. In certain embodiments, the solution is allowed to react at a temperature of between about 15° C. and about 30° C. for a period of between about 1 and about 24 hours, or at a temperature of between about 20° C. and about 25° C. for a period of between about 1 and about 5 hours, or at room temperature for a period of about 5 hours.

Implants made with a hydratable keratin solid offer particular advantages over other implants, especially in implants that involve a large amount of material, such as breast or gluteal pad implants. In a preferred method of use, the hydratable keratin solid in powder or fiber form may be added to an envelope interior prior to insertion, and water may then be injected into the envelope after implantation, thus forming the hydrogel in situ. In the practice of this embodiment, the implant envelope containing a dry solid will have a small volume relative to the size of the final implant, thereby allowing a relatively small incision for insertion of the implant. In certain applications, it may be more advantageous to implant an empty envelope, again allowing for a relatively small incision, to form a hydrogel outside the body and then injecting the hydrogel into the envelope through a large bore needle, for example. It is also understood that implants may be formed with the hydrogel in place in the envelope prior to implantation. Such implants are advantageous as intervertebral disc, nucleus and annulus replacements or repairs.

Tissue expanders made with a hydratable keratin solid offer particular advantages over other tissue expanders, especially tissue expanders which require volume adjustments which are made through an externally filled tube. The use of an external filling is often uncomfortable and inconvenient for the patient, and can lead to an increased incidence of infection. In a preferred method of use, the hydratable keratin solid in powder or fiber form may be added to a tissue expander envelope interior. The permeation of body fluids through the envelope can be controlled through the use of certain materials and engineering principle well known to those skilled in the art. The control of the diffusion rate has the effect of controlling the hydration rate of the keratin solid and thus, the expansion rate of the hydrogel thus formed. The expansion rate can thus be controlled in-situ, without the use of an external fill tube. This method of use would lead to a more comfortable and convenient tissue expander with lower incidence of infection. Alternatively, the hydration rate of the keratin solid can be controlled by controlling the absorbency of the keratin solid during manufacture as described herein. A solid tissue expander formed from an absorbent keratin solid with a controlled absorption rate would have the advantage of expanding its volume at a controlled rate in-situ, and thus providing the same advantages as noted previously.

In certain embodiments implants can be made using a keratin hydrogel formed using a method that does not include a hydratable keratin solid stage. An implantable keratin hydrogel can be made by a process beginning with providing a keratinous material from a biological source, such as hair, fur, feathers, hooves or nails, most preferably human hair, and oxidizing the hair or other keratin material. The oxidized hair can be suspended in a base solution, such as an ammonium hydroxide solution, for example, wherein the solution contains thioglycolate. The solution may then be heated, and stirred under an inert environment such as an $N_2$ environment, for example. Although the use of a nitrogen environment may be preferred for certain embodiments, any oxidatively inert gas such as argon or helium, for example, may also be used. A swelled fraction of keratin gel can be separated from the suspension and added to an oxidizing agent such as hydrogen peroxide or peracetic acid, for example. Alternately, the swelled fraction can be exposed to ambient air. The gel can be allowed to stand in the oxidizing environment, thereby forming a crosslinked hydrogel. This method of forming a crosslinked gel is described more completely in U.S. Pat. No. 5,932,552 incorporated herein by reference.

The implant can be made by filling the envelope interior either before or after implantation. In implants filled after implantation, the implant can be rolled into a small profile shape and inserted through a small incision into the interior of a breast or other organ or area to receive an implant. As is well known in the art, an incision for breast replacement may be made in the navel, or near the edge of a mastectomy scar, for example, and incisions for augmentation may also be made in the crease at the bottom of the breast or around the areolar area of the breast. The envelope can then be unrolled and the hydrogel injected through a large bore needle, using the same incision used to insert the envelope. The injection can be made into a self-sealing port provided in the envelope. Such embodiments are also suitable for intervertebral disc, nucleus and annulus replacement and repair.

Hair is a preferred source of keratin for the present invention. In particular, human hair is a preferred source. In one method, hair is harvested from the intended implant recipient. While any human hair is believed suitable as a source, the use of hair from the intended recipient may provide a psychological and allergenic advantage relative to hair from other sources.

An object of the present invention is to provide for implants which accomplish intervertebral disc replacement and repair. Such replacement and repair can be to the entire disc or to the nucleus or the annulus associated with the disc. Replacement and repair can be accomplished through the use of keratin based products of the invention by themselves and in combination with single or multiple envelope arrangements. Initially repair and/or replacement can also be accomplished with single or multiple layers of the keratin based product of the invention with and without nonwoven felts comprised of a synthetic polymer and/or a keratin based product of the invention. An example of non-woven materials that may be used are described in U.S. patent application Ser. No. 09/587,157 incorporated herein by reference.

The replacement and repair implants can be shaped to match the portion of the annulus that is being replaced. Further these implants can also transport drugs, living cells, co-factors and/or other materials that can stimulate healing of damaged structures. Other features and advantages of the invention are presented in the specification and in the claims.

DETAILED DESCRIPTION OF THE INVENTION

Figure 1A:
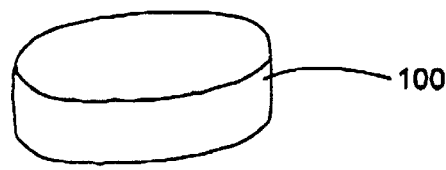
FIGS. 1a–1e depict embodiments of the invention including one or more layers which can be used for intervertebral disc replacement or repair.

The present invention arises from the discovery by the present inventors that prosthetic implants, or implants to replace or augment soft tissues in the body, especially in the human body can be made from a keratin material, and in a most preferred embodiment, from human hair. The implants described herein offer numerous advantages over other implants, especially silicone, saline, or even autogenous fat cells. These advantages include that the keratin gel implants are less toxic than silicone implants should a leakage occur, keratin gel implants have a more natural look and feel than saline implants, and keratin implants require an incision or injection only at the site of implant, and do not require a second invasive procedure for harvesting tissue such as fat cells, for example.

Example 1
Implants Utilizing Keratin Hydrogel from Solid Precursor

The present example describes implants having a keratin hydrogel contained within an envelope, where the keratin hydrogel is formed from a solid, keratin hydrogel precursor which forms a keratin hydrogel upon the addition of water. The solid precursor form of keratin derived implant material may be used in several ways, depending on the need of the practitioner. For example, the solid may be hydrated prior to placing the keratin filler into an implant envelope. In the practice of this method, one would be able to determine precisely the volume of the implant filler prior to placing the filler in the envelope of the implant. The hydrated gel could then be injected into the envelope either before or after the envelope is implanted. It is understood that the invention would include prepackaged, sterile, prefilled, sealed implants as well as a package that includes various sized envelopes and a separately packaged hydrogel, or hydrogel precursor.

In certain embodiments, a solid precursor may be added directly to an implant envelope and subsequently hydrated in the envelope either before or after the envelope is implanted. Again, hydrating the keratin after implantation, or injecting the hydrated gel into the envelope after implantation both allow a much smaller incision to be made, and allow the injection through the same incision of either water or hydrogel. This embodiment of the invention would include a packaged implant with a premeasured amount of solid hydrogel precursor, or would include the separate packaging of envelopes and solid precursor.

In the present example, a solid hydrogel precursor can include protein having an ionizable pendant group, such as sulfonic acid, or cysteic acid, which can be derived from an oxidized protein disulfide linkage. A preferred source of protein is keratin, preferably keratin obtained from hair, and most preferably keratin obtained from human hair. While hair is a preferred source of keratinous material, other keratinous materials are also believed suitable for use in the present invention. Examples of other sources include animal hair or fur, skin, hooves, feathers, beaks, feet and horns. The patient or a human donor are some preferred sources of hair, as hair from these sources is most likely to result in a non-antigenic product, although animal hair may be acceptable for many individuals. In one method according to the present invention, hair is provided, preferably clean and unbleached. In another method, the hair is washed with Versa-Clean ™ (Fisher Scientific, Pittsburgh, Pa.), or other cleaners, rinsed with deionized water, and allowed to dry.

In a preferred method of preparing a solid hydrogel precursor, cleaned hair can be oxidized in peracetic acid or another suitable reagent such as $H_2O_2$. One method utilizes between about 1% to 32% peracetic acid, at a temperature between about 0 degrees C. and 100 degrees C. for between 0.5 and 24 hours. In one method, about 1 weight/volume percent peracetic acid is used. One method treats 30 grams of hair with 500 mL of 4% peracetic acid at 4 degrees C. for 21 hours. Another method treats the hair at room temperature for 24 hours. Yet another method treats the hair at about 90 degrees C. for about 10 hours. In a preferred method, the hair is treated by heating the hair in the oxidizing agent for between about 1 and 4 hours at a temperature between about 20 and 100 degrees C. In a more preferred method, the hair is treated by heating the hair in the oxidizing agent for between about 1 and 2 hours at a temperature between about 80 and 100 degrees C. In a most preferred method, the hair is treated by heating the hair in about 2 weight/volume percent oxidizing agent for about 2 hours at a temperature of about 100 degrees C. The oxidation is believed to cleave a significant portion of keratin disulfide bonds forming cysteic acid residues. The sulfonic acid groups are believed to be hydrophilic in nature and will ionically bond to cations later in the process, forming a salt of the keratin and cation.

After oxidation, the keratin solid can be recovered from the oxidizing liquid using filtration or other suitable methods such as centrifugation or decantation. The recovered, oxidized solid may be washed with water or any other suitable liquid such as an alcohol, including methanol or ethanol, for example, to remove the excess oxidizing agent.

The solid fraction can be suspended in a suitable solvent. The solvent should be capable of at least suspending the hair or keratin solid and keeping the solid sufficiently swelled for subsequent reaction. The solvent is preferably a non-aqueous solvent, as the presence of water can contribute to hydrolysis of peptide backbone bonds of the protein product, which can result in an inferior product. The solvent should also be able to solubilize the later added cation. One group of suitable solvents includes alcohols such as methanol and ethanol. Other solvents such as ether, tetrahydrofuran (THF), and acetone may also be suitable as solvents. The solvent used is preferably volatile to promote evaporation from the final solid product.

The hair or keratin solvent suspension may then have the pH titrated upward to at least about pH 7, or preferably to a pH at or above the pKa of the sulfonic acid groups of the protein. This increased pH acts to ionize or deprotonate the sulfonic acid groups and allows ionic interactions with cations. The cations are preferably produced by including a base in the solution, preferably a monovalent base, or a base that provides a monovalent cation in solution. Preferred bases include, but are not limited to ammonium hydroxide, sodium hydroxide and potassium hydroxide.

The keratin suspension can be heated for a time and temperature sufficient to swell the keratin structure and promote neutralizing of the sulfonic acid sites with the provided cation. In a preferred method, the keratin is suspended in ethanol and boiled between about 0.5 hours and 12 hours in the presence of the cation. More preferably, the keratin is suspended in ethanol and boiled between about 0.5 hours and 3 hours in the presence of the cation. In one method, the keratin is suspended in ethanol and boiled for about 1 hour in the presence of the cation. Boiling for too long a time period is believed to lead to a final, partially solubilized or mushy keratin which may result from degradation of the peptide backbone. A partially solubilized keratin product is less preferred due to the greater difficulty of grinding the keratin.

After boiling, the keratin is preferably allowed to continue to react with the provided base cations at lower temperature and with stirring. The lower temperature reaction preferably takes place at a temperature of between about 15 and 30 degrees C. for between about 1 and 24 hours. More preferably, the lower temperature reaction takes place at a temperature of between about 20 and 25 degrees C. for between about 1 and 5 hours. In one method, the keratin suspension is allowed to react with stirring at room temperature for about 5 hours.

After ion exchange at lower temperature, the solid salt can be separated from the solvent using any suitable method such as filtration. The solid is preferably washed with a solvent that may be the same solvent as that used in the reaction. Washing the keratin removes excess base, which is preferably removed to make the keratin solid neutral.

After filtration and washing, the keratin can be dried by a method such as evaporation under vacuum. In one method, the keratin is dried at room temperature under about 5 mm Hg vacuum for about 2 hours. The dried keratin is preferably somewhat brittle, which can result in a better product after grinding. The dried keratin can be shredded into fibers or can further be ground into a powder. The dried keratin can be directly ground into a powder using a mortar and pestle, a ball mill, or other means of breaking down or comminuting the dried keratin into particles. Solid keratin hydrogel precursor can be provided in either fibrous or powder form for use in the implant.

The solid keratin hydrogel precursor is capable of absorbing many times its own weight in water. In one test, fibers were shown to absorb an average of 13 times their weight in water at 21.5° C., and may absorb up to 20 times. The absorbed water is chemically bound to the keratin through acid-base interactions such as hydrogen bonding. This results in a stable, viscoelastic hydrogel from which the water cannot be separated by normal mechanical means such as centrifugation or compression.

A patient, the intended recipient, can be prepared for the operation and a small incision made at the breast or other area such as by way of example only, the intervertebral disc area, to receive an implant. The envelope can be rolled into a cylinder or other small shape to decrease the profile and the compacted envelope inserted through the incision. The envelope can be allowed to attain a less constrained shape well known to those skilled in the art, such as a meniscus or soft disc shape. Leaving the envelope empty or containing only a solid hydrogel precursor can greatly decrease the volume of the envelope during insertion. Decreasing the volume can greatly decrease the implant profile and the required incision size. By waiting to inject any fluid into the implant until after implantation, a more minimally invasive procedure can be performed. In one method, the envelope includes a self-sealing injection port in the envelope wall. A large hypodermic syringe can be used to inject the fluid into the self-sealing port. The large hypodermic is preferably inserted through the already formed incision in the breast or other tissue, to avoid the need for an additional puncture. In embodiments having a keratin hydrogel precursor in the envelope, the injected fluid can be water, thus forming the hydrogel in situ. In embodiments using a preformed hydrogel, the hydrogel can be injected through a preferably large bore needle and into the envelope interior. While the hydrogel can be quite viscous, the needle bore can approach the size of the incision in some embodiments. After implantation, the incision can be closed and allowed to heal.

Such implants can be impermeable, semipermeable and permeable to bodily fluids. Thus for semipermeable and permeable implants, the implant can come to a desired shape and size over time.

Example 2
Tissue Expanders Utilizing Keratin Hydrogel from Solid Precursor

The present example describes tissue expanders having a keratin hydrogel contained within an envelope, where the keratin hydrogel is formed from a solid, keratin hydrogel precursor which forms a keratin hydrogel upon absorption of body fluids. A variety of different sized tissue expanders can be provided by varying the size of the envelope and the amount of keratin hydrogel precursor. In addition, the rate at which the tissue expanders reached their final volume can be varied by controlling the diffusion rate of body fluids into the tissue expander, or by varying the absorbency of the dry keratin solid, as described herein.

A patient, the intended recipient, can be prepared for the operation and a small incision made in or near the breast or other area to receive a tissue expander. Placing the tissue expander in its dehydrated form allows for the implant to absorb body fluids through the envelope at a controlled rate, thus increasing in volume at a controlled rate. The volume expansion occurs in-situ, after the incision has been closed, and provides a more comfortable and convenient implant when compared to conventional treatments. A lower incidence of infection would result from having a closed incision without the need for an external fill tube as in conventional tissue expander products.

Example 3
Implants Using Keratin Hydrogel Formed from Keratin with Added Hydrophilic Groups and with Reformed Crosslinks In the present example, an alternate embodiment is described, a keratin hydrogel that is provided using a method that does not involve adding water to a solid keratin hydrogel precursor. The keratin material may be obtained from the same sources as described in Example 1, and preferred source of keratin is human hair. In one method, hair is provided, preferably washed and unbleached. The hair is harvested from a human or animal source. The patient or another human donor is a preferred source of hair, as hair from these sources is most likely to result in a non-antigenic product, although animal hair may be acceptable for certain individuals that do not have animal product allergy problems. In one method, the hair is washed with Versa-Clean TM (Fisher Scientific, Pittsburgh, Pa.) or other suitable cleansing agent, rinsed with deionized water, and allowed to air dry.

The hair can be oxidized in peracetic acid or another suitable reagent such as $H_2O_2$. A preferable treatment utilizes from 1% to 32% peracetic acid, at a temperature between about 0 degrees C. and 100 degrees C. for between 0.5 and 24 hours. One method treats 30 grams of hair with 500 mL of 32% peracetic acid at 4 degrees C. for 24 hours. This treatment with peracetic acid is believed to partially oxidize the naturally occurring disulfide linkages to produce a protein with cysteic acid ($—CH_2SO_3H$) residues.

The hair is recovered, preferably with filtration through a coarse fritted glass filter, and rinsed numerous times with deionized water until the rinse solution has a pH of 6.0 or higher. The hair can then be dried in a vacuum oven at between 20 degrees C. and 50 degrees C. for between 0.5 and 5 days. One method dries the hair in a vacuum oven at 40 degrees C. for several days. The dried hair can then be pulverized and ground into a fine powder. One method of grinding the hair uses a ceramic mortar and pestle.

The keratin powder can be suspended in a sulfhydryl solution such as an ammonium thioglycolate solution, for example. In one method, pulverized keratin powder, derived from hair as described above, is suspended in about 3N ammonium hydroxide containing thioglycolate. About six grams of keratin powder can be added per 75 mL of 3N ammonium hydroxide solution. The strength of ammonium hydroxide is preferably about 3N and the preferred concentration of ammonium thioglycolate is from about 2 to about 20 ml (as thioglycollic acid) per 75 ml of ammonium hydroxide, or about 11 ml thioglycolate per 75 ml ammonium hydroxide in certain embodiments. The suspension can then be heated for a time sufficient to solubilize the soluble fraction of the hair. The suspension in one method is heated to between 50 degrees C. and 90 degrees C. for between 1 and 24 hours, followed by cooling. In a preferred method, the suspension is heated to about 60 degrees C. for about 4 hours and cooled to room temperature.

Applicants believe this treatment cleaves the remaining disulfide linkages to produce cysteine residues in the protein structure. At this point, the keratin protein is believed to contain sulfonic acid, sulfhydril and cystine-thioglycolate containing residues. The ratio of sulfonic acid residues and sulfhydril residues can be controlled by varying the time, temperature, and concentration of oxidant in the peracetic acid treatment step previously described. The presence of sulfonic acid residues imparts a hydrophilic property to the hair as well as to the final hydrogel product.

After the treatment described above, a keratin fraction resistant to the treatment remains, consisting primarily of beta keratin. This fraction is insoluble in the suspension and is removed in one method by centrifugation at about 10,000 g for about 10 minutes. The insoluble fraction is set aside and is available for other uses. A thick, jelly-like supernatant remains which includes a soluble keratin fraction. The supernatant is collected and used to make the implant material described herein.

The supernatant is preferably purified, using a method such as dialysis. A preferred method uses dialysis against running water using a dialysis membrane (Spectra/Por TM) having a cutoff of about 8000 MW. The resulting solution is preferably concentrated to a concentration of about 0.1 grams per mL.

The keratin in solution is now ready for crosslinking to form a hydrogel. In a preferred method, an oxidizing agent is added to the keratin to crosslink the keratin proteins. Preferred oxidizing agents include oxygen, hydrogen peroxide, organic peracids, peroxy carbonates, ammonium sulfate peroxide, benzoyl peroxide, and perborates. Hydrogen peroxide is preferably added to the keratin solution at about 0.5% to about 1.0% w/v, mixed well, and allowed to stand at room temperature for several days. A preferred standing time is about 3 days. The freely flowing solution slowly thickens and converts to a crosslinked hydrogel after about 72 hours.

The insoluble keratin fraction from hair is thus partially oxidized so as to have the protein backbones interconnected with disulfide linkages and having sulfonic acid residues. The partially oxidized keratin is treated with a reducing agent to cleave some or all of the remaining disulfide bonds, forming thiol groups and cystine-thioglycolate groups and to solubilize more of the keratin proteins. After removing the insoluble fraction, the keratin is oxidized to allow the formation of disulfide crosslinks. Disulfide crosslinks are thus reformed. As used herein, the term "reformed" refers to crosslinks broken and formed later in time, where individual linkages later formed could be, but are not necessarily, between the same amino acid cysteine pairs.

A crosslinked, pure keratin hydrogel results. The hydrogel has sulfonic acid groups which are hydrophilic and bind water within the hydrogel. The number of sulfonic acid groups corresponds to the degree of keratin oxidation in the partial oxidation step.

In one method for implanting the envelope, the hydrogel is formed by adding the oxidizing agent to the keratin supernatant outside of the envelope followed by mixing. After a time period, the mixed hydrogel and oxidizing agent or other crosslinking agent can be injected into the implant envelope. In some procedures, the envelopes are prefilled with keratin hydrogel prior to packaging the implant. In some procedures, the envelopes are filled with keratin hydrogel by injection only after implantation of the envelopes. In some procedures, the oxidizing agent and keratin supernatant are mixed close to the time of the surgical procedure, and the mixture injected soon after mixing, before the mixture becomes very viscous. In these procedures, the mixture can be allowed to thicken in situ.

The present invention includes hollow implants which can have a thicker envelope wall than those commonly used in breast implants. A keratin hydrogel can be used to fill any hollow implant envelopes known in the art, including penile implants, testicular implants, chin implants, intervertebral implant including but not limited to intervertebral disc, nucleus and annulus implants, and gluteal pad implants.

Numerous advantages of the invention covered by this disclosure have been set forth in the foregoing description. It will be understood, however, that this disclosure is, in many respects, only illustrative. Changes may be made in details, particularly in matters of substitutions of chemically or biologically equivalent substances, or in the order of steps in certain methods without exceeding the scope of the invention. The invention's scope is, of course, defined in the language in which the appended claims are expressed.

Example 4

Intervertebral Disc Space Repair and Replacement Implants

The present embodiments relate to intervertebral disc space repair and replacement implants. More particularly, by way of example only, disc, nucleus and annulus replacement implants and repair implants are discussed. It is to be understood that the teachings of the rest of the specification apply equally well to the embodiments presented in this Example 4.

In many patients suffering from back pain, disc extrusion or nerve impingement, it may be desirable to provide support for the annulus, if present. The annulus, in general, contains the nucleus, which provides vertical support against compressive loads and maintains the disc height. When a disc nucleus degenerates, it loses water, becomes weakened, and thereby does not provide sufficient vertical support for the body weight. The annulus can provide some lateral support for a normal and also for a weakened disc nucleus. However, it does not support vertical loads very well. If the nucleus becomes too weak, or if the annulus is damaged through injury or disease, the annulus may not provide sufficient structural support for the body weight, and a portion of a disc nucleus can be extruded from within the intervertebral space, forming a "herniated disc."

Thus, surgical repair, reconstruction or replacements of herniated discs, eroded discs, and missing discs is often a challenging problem. Annulus repair is also a solution which has been given little or no attention. However, using keratin-based materials, and encapsulations of these materials, as described throughout this specification, significant improvement in the function of the disc, nucleus, and/or annulus can be provided. Thus, this invention includes implantable disc replacements and repairs having keratin based materials therein. Disc replacement can comprise a nucleus replacement, an annulus replacement, or both. Depending on the subject's need, the entire annulus, the nucleus or a portion thereof can be replaced or repaired.

Nucleus Replacements or Repair—Generally

Nucleus replacements can include gels and/or gels in flexible containers. In certain embodiments in which a portion of the natural disc is functional, only a damaged or ineffective, part of the original nucleus need be replaced. In other embodiments of this invention, when a substantial portion of the nucleus is ineffective, it can be desirable to replace more of the nucleus. In further embodiments, it may be necessary to replace the entire original nucleus with an artificial disc replacement. Nucleus replacements of this invention can include keratin products. Keratin products include non-woven keratin, keratin gels, and keratin products which contain keratin peptides. Examples of keratin peptides that may be included are described in U.S. patent application Ser. No. 09/330,550, incorporated herein by reference.

Depending on the site of nucleus replacement, the material can desirably be selected to resist the pressures to be encountered at that site. For example, the lower lumbar spine typically is exposed to greater vertical stresses than the cervical spine. This is, in general, because the body weight and muscle forces are greater at the lumbar spine than at the cervical spine, which typically needs only to support the weight of the head. Additionally, during flexion, the loads on the posterior annulus are greater than on the anterior annulus.

Therefore, in certain embodiments, it can be desirable to provide nucleus replacement materials having stress-strain relationships that can minimize the likelihood of the portion of the nucleus from becoming completely compressed. In certain embodiments, a material having a stress-strain relationship wherein there is relatively little compression with increased compressive stress can be made by providing a denser material or by providing an incompressible material such as a hydrogel in a relatively rigid containment device, or capsule. Alternatively, in situations in which relatively less stress needs to be supported, a less dense non-woven material or a gel in a relatively more flexible containment device can be used.

A. Nucleus Replacements or Repairs of Non-Woven Keratin

Non-woven keratin nucleus replacements of embodiments of this invention can be in the form of a fibrous network or felt. The non-woven product can be formed either as single layer material or as multiple layered sheets. In some embodiments, different layers of keratin material can be used. For example, one sheet of keratin can be formed having a selected fiber size, density and/or degree of sulfonation or other charge bearing moieties. A second sheet can be formed having a different fiber size, density, degree of sulfonation and/or other characteristic. Such laminates can thus have certain selected properties on one face and other properties on the other face. In other embodiments, multiple layers of keratin material can be used, in which different layers can have different selected charge, charge density, density, fiber length or other properties.

In alternative embodiments, the keratin non-woven nucleus repair or replacement can also have natural or synthetic polymer materials as laminates and/or as non-woven co-precipitates. Laminates can be made by preparing separate layers of polymer materials and then adhering them together. Laminates can also be made by forming a subsequent layer on top of an already formed layer. In certain embodiments, laminates can be made having three or more layers of polymer material. For example, a laminate can be prepared having a top layer of keratin, a middle layer of a synthetic polymer, and a bottom layer of keratin. Such three-layered laminates can provide the advantages of keratin on the surface of the repair or replacement, while providing desirable properties such as mechanical strength and flexibility to the disc replacement. In similar fashions, multiple layered laminates can be manufactured to have a variety of properties in each lamina. Additionally, with multiple layers of a synthetic polymer, each layer can have a different orientation in order to achieve certain mechanical functionality such as enhanced strength and other properties.

Figure 1D:
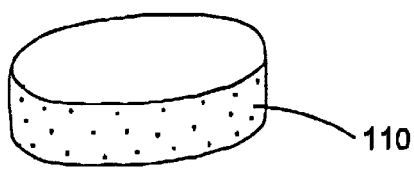
Figure 1B:
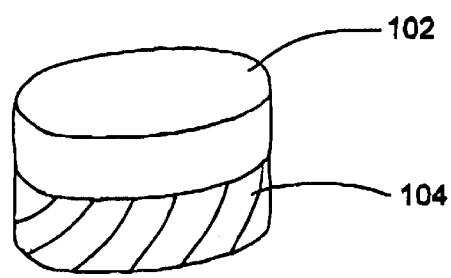
Figure 1E:
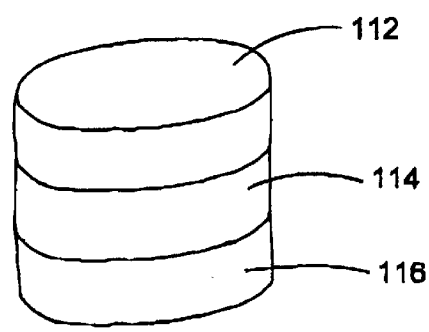
Figure 1C:
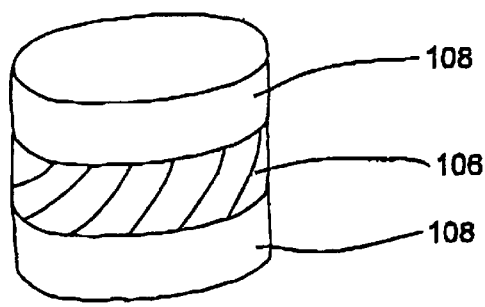

FIGS. 1a–1e depict embodiments of this invention. FIG. 1a depicts a non-woven keratin sheet 100 having a uniform thickness. FIG. 1b depicts a bilayered nucleus replacement having a layer of keratin 102 and a layer of another polymer 104. FIG. 1c depicts a multilayered nucleus replacement comprising a keratin layer 106 and polymer layer 108. FIG. 1d depicts a co-precipitated nucleus replacement 110. FIG. 1e depicts a multilayered nucleus replacement having multiple layers 112, 114, 116 of keratin material having different properties.

Co-precipitates can be made by preparing solutions of the keratin material and other polymer material(s) separately, mixing the solutions together, and then drying the resulting mixture to form a felt that contains both keratin and the other polymer(s). The resulting non-woven product therefore contains desirable features of keratin, including being relatively inert, as well as desirable features of the non-keratin polymer(s). Such non-keratin polymers referred to in this specification can include by way of example only polyester, polyethylene, poly(tetrafluoro)ethylene, polypropylene, silicones and other polymers known in the art.

Uses of Non-Woven Keratin Nucleus Replacements or Repair

In certain embodiments, felts comprising keratin can be provided having a shape that can be either pre-formed or can be prepared at the site of surgery to conform to the desired intravertebral space. The disc replacement can be provided as a sheet of uniform thickness, with top and bottom faces being substantially parallel, and can advantageously be used in situations in which the faces of adjacent vertebral bodies are substantially parallel. In alternative embodiments, non-woven material can be provided that has unequal thickness to accommodate non-parallel surfaces of adjacent vertebral bodies.

For example, in the lumbar and sacral spine, the dorsal aspects of the vertebral bodies are generally closer together than the ventral aspects. Thus, a wedge-shaped nucleus replacement can be used with a thinner aspect of the disc replacement positioned near the dorsal aspect of the vertebral bodies, and a thicker aspect can be positioned near the ventral aspect. Thus, when in use, the normal curvature of the lower lumbar spine can be well supported by the disc replacement.

In other locations, for example in the thoracic spine, the ventral aspects can be closer together than the dorsal aspects. In these situations, it can be desirable to position a wedge shaped nucleus replacement wherein the thinner portion of the disc replacement is near the ventral aspect and the thicker portion is positioned near the dorsal aspect.

In yet other embodiments, in which the intervertebral space is more uniform in thickness, it can be desirable to provide nucleus replacments having more uniform thickness.

In certain situations in which the intervertebral space is irregularly shaped, a surgeon can adapt a pre-formed nucleus replacement to suit the patient's particular needs. Thus, if a vertebral body defect results in an abnormally large depression in one region of a vertebral body, the surgeon can select a relatively thick replacement and remove portions of the replacement so that the inserted replacement can fit more beneficially within the patient's intervertebral space.

Example Embodiment of Intervertebral Disc Replacement—Layered Sheet Material

FIGS. 2a–2d depict embodiments of this invention wherein non-woven keratin material is designed to support the load.

Figure 2A:
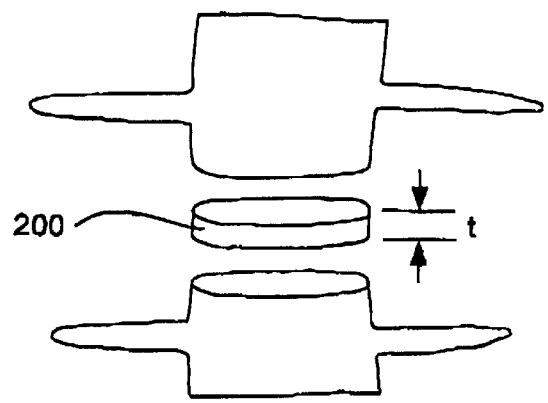
FIGS. 2a–2d depict embodiments of the invention wherein nonwoven keratin material is designed to support a load, such as the load exerted on the spinal column.

FIG. 2a depicts a uniform non-woven nucleus replacement 200 of this invention. The nucleus material has an approximately circular area and a thickness designed to provide cushioning support between two adjacent vertebral bodies.

Figure 2B:

FIG. 2b depicts an alternative embodiment in which the non-woven nucleus replacement 202 has non-uniform thickness.

Figure 2C:
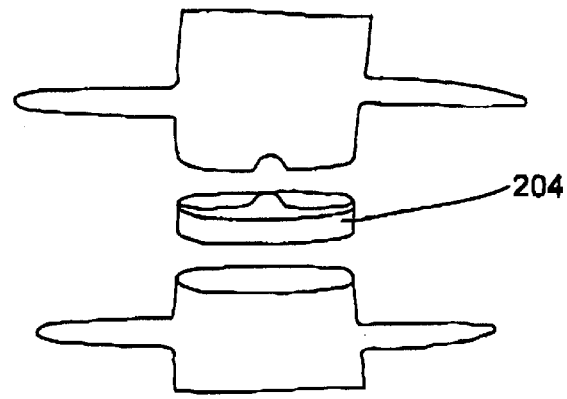
Figure 2D:
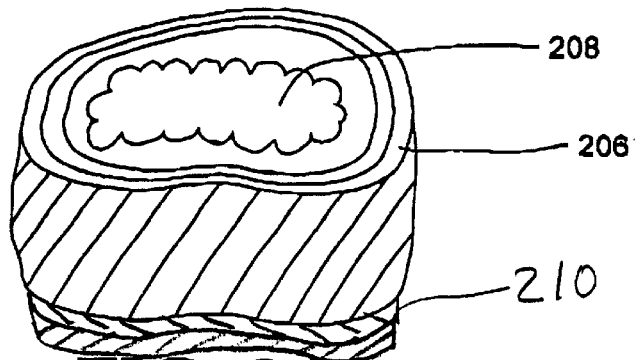

FIG. 2c depicts another embodiment of this invention in which the non-woven nucleus replacement 204 has an irregular thickness to accommodate an uneven intervertebral space.

Individual sheets of a keratin-based material will be layered and molded into the shape of an annulus fibrosis 206. Concentric layers of a keratin-based sheet material will be applied to one another about a central, vertical axis until a thickness of approximately 1 to 2 cm is achieved. The layers will be formed such that there is an outer layer and an inner layer. Approximately 10 to 20 individual layers will be used. Thus each of the inner layer and the outer layer can be formed of one or multiple individual layers or sheets of keratin-based material. Each sheet or layer can be comprised of the non-woven or the woven type with keratin-based material deposited thereon as described herein. For strength the alternating sheets can have directionally different structural strengths depending on the orientation of the non-woven or woven material and how it is formed. Thus if the elements or fibers of the material have directionality, the sheets can be combined so that the directionality of each sheet is different from the next. The sheets can be formed one and then the next on top of the first in order to make the layers or the sheets can be glued together with glues that are known in the art.

It is to be understood that if an inner layer and an outer layer structure is formed, that the inner layer would be more favorably compatible with the below described keratin-based hydrogel 208, while the outer layer could for example be more structurally capable of carrying the load due to the strength and number of the sheets that comprise the outer layer. Also for such an embodiment which is meant to be a full or partial disc replacement implant, the disc implant can have an upper and a lower portion. In FIG. 2c the lower portion is shown. The upper portion would be similar. In FIG. 2c, the lower portion includes sheets of non-woven or woven material or both, some or all of which have deposited thereon keratin-based materials. In addition, as with the annulus, the individual sheets can have directionally different structural properties. As indicated below, either or both of the sheets and the hydrogel can include one or both of cells and/or growth factors. The inner volume of the layered material will be filled with a keratin-based hydrogel 208. The prosthetic intervertebral disc will be positioned in the place of an excised, degenerated intervertebral disc and bonded to the endplates via fibrous ingrowth. The layered keratin-based material and keratin-based hydrogel may or may not contain cells and/or growth factors. The growth factors may or may not induce host cells to migrate or differentiate and produce a fibrous ingrowth between the layered keratin and endplate, and produce hydrophilic proteoglycans. In addition, the impregnated cells or host cells may produce connective proteins to secure the the keratin-based layers to the endplate. Also, the impregnated cells or host cells may produce hydrophilic proteoglycans.

The resulting intervertebral disc prosthesis should be meet the following kinematic requirements: +/−3 deg flexion, +/−5 deg flexion/extension, +/−3 deg lateral bending. In addition, the disc must be able to withstand 1200 N of compression and 2.5 MPa of internal pressure. The approximate dimension of the prosthesis should be 6 to 20 mm in height, 30 to 70 mm in width, and 30 to 50 mm in depth.

Adjuncts to Keratin Materials

In certain embodiments, it can be desirable to include other, non-polymer materials with keratin materials. For example, it can be desirable to include drugs, cells, co-factors, and/or other materials that can stimulate healing of damaged structures. In certain embodiments, it can be desirable to include antiinflammatory agents, such as non-steroidal antiinflammatory drugs (NSAIDs) to decrease infiltration of undesirable inflammatory cells into the intervertebral space. In other embodiments, it can be desirable to include certain cytokines, such as interleukins, bone growth promoting peptides, keratin peptides, vitamins, enzyme inhibitors and/or other materials known in the art.

Keratin Nucleus Replacements and Repair Containing Living Cells

In yet other embodiments, it can be desirable to include living cells in the nucleus replacement or repair. In situations in which the disc collagen has been damaged, chondrocytes can be provided within the nucleus replacement material to provide a source of new chondrocytes. When chondrocytes are stimulated to grow and produce new collagen the intervertebral space can become augmented with naturally occurring collagen.

In other embodiments, wherein bony portions of the vertebral bodies are damaged due to injury or disease, it can be desirable to provide a keratin nucleus replacement containing osteoblasts or osteocytes, either alone or along with osteogenic materials such as bone morphogenetic proteins (BMPs) which can promote cell growth and division or differentiation and secretion of extracellular materials needed for regrowth of the missing tissue.

In these embodiments, after implantation, the keratin materials can provide growth scaffolds for the proper growth of chondrocytes, fibrochondrocytes, fibroblasts, osteoblasts and/or osteocytes. Once the intervertebral space has been repopulated with proper cells, those cells can be made to differentiate and produce cartilage, bone or other structural tissues.

In certain embodiments, the use of fibroblasts, fibrochondrocytes, chondrocytes, osteoblasts and osteocytes can be desirable to promote the healing and regrowth of damaged or injured vertebral bodies and nuclei.

In these situations, it can be desirable for the keratin material to have a biological lifetime that is compatible with the replacement of cartilage. Thus, as new cartilage grows, the keratin can be biodegraded and removed, making more room in the intervertebral space for newly formed cartilage.

E. Keratin Gel Nucleus Replacements and Repairs

Keratin gels can be desirable in situations in which a relatively rigid nucleus replacement is not desired. Such situations include those portions of the spine where flexibility is desired, such as the cervical spine, or in areas in which vertical stresses change widely during, for example, postural changes.

Keratin gel-based nucleus replacements can have different forms. For example, in certain embodiments, a gel by itself can be used. Being a protein, keratin has some intrinsic strength and therfore resistance to compression. Using a keratin gel along with non-woven keratin material can provide a degree of flexibility as well as flexibility to the disc replacement. In certain embodiments, keratin gels can be used without additional non-woven keratin material. In other embodiments, a keratin gel can be placed within a capsule or envelope.

The load bearing capacity of a keratin gel-containing capsule is related to intrinsic resistance by the gel of a compressive load and the ability of a capsule or envelope to contain the pressure within the capsule or envelope generated by the load. By varying the composition of the gel and the size and configuration of the capsule, different load and flexibilities can be provided for a disc replacement. For example, a stiff keratin hydrogel can be used with a relatively weak capsule to provide an equivalent load bearing capacity as a weaker keratin hydrogel and a relatively stronger capsule.

1. Gels without Capsules—Generally

Certain embodiments of this invention include keratin hydrogels as nucleus replacements or repairs having no containment device. For these embodiments, it can be desirable for the gel to have sufficiently low bioresorbability and sufficient stability so that after placement, the gel remains within the interveterbral space without any additional structural support. Keratin gels used in this way desirably have sufficient physical and chemical characteristics so that when hydrated to their proper volume in situ, the gel tends to resist water expression and compression of the gel, thereby decreasing the thickness of the disc replacement or repair and resulting in a close approximation of the vertebral body surfaces.

To resist such water expression and gel compression, in certain embodiments, gels of this invention can have sufficiently large numbers of electrical charges to retain water through Van der Wahls forces, ionic interaction or dipole-dipole interactions. Because keratin gels comprise proteins made of amino acids, polar and/or charged amino acids can take part in forming hydrated gels. Additionally, because keratin has numerous cysteic acid residues that can be oxidized to form sulfonic acid residues, the degree of sulfonation can affect the ability of a hydrogel to retain water. By increasing the number of sulfonic acid residues in a strand of keratin, more negatively charged moieties can be present. Sulfonic acid groups, being charged, can bind water molecules, dissolved inorganic ions such as Na+(sodium), K+(potassium) and other cations.

In solutions of water and ions, such as physiological media including the extracellular milieu, cations are typically hydrated through Van der Wahls forces, ionic interactions and/or dipole interactions. A water molecule is made of one oxygen atom and two hydrogen atoms. The two hydrogen atoms are covalently bonded to the oxygen atom with bond angles relative to each other of about 109°. Oxygen is more electronegative than hydrogen, so the hydrogen oxygen atoms do not equally Ashare@ the electrons that make up the oxygen hydrogen covalent bond. Rather, the oxygen tends to attract the electrons more closely to its nucleus, and results in a molecule having a net dipole, with the oxygen atom having a net partial negative charge and the two hydrogen atoms each having a net partial positive charge. Thus, in liquid media having cations, water molecules tend to arrange themselves with the electronegative oxygen atoms being closer to the positive charges of the cations, thus tending to neutralize the charge separation between the ion and the water molecule. A single ion is like a Ahub@ and the water molecules are like Aspokes@ of a wheel. This results in a Ashell@ of water molecules surrounding the Asolvated@ cation. As a result, the hydrogen atoms, with their relative electropositivity, tend to be oriented centrifugally, or away from the solvated cation. Thus, a first shell of water tends to have a net partial positive charge.

A second shell of water molecules can be arranged around the first shell. In the second shell, as described above, the oxygen atom is relatively electronegative and tends to remain close to the hydrogen atoms of the first shell. Thus, the second shell has water molecules arranged as spokes with the oxygen atoms nearer the solvated ion and the hydrogen atoms more distant. Subsequent shells of water can be formed, but as more shells are present, the orientation of the water molecules becomes less ordered, so that at some distance from the solvated cation, the water molecules are attracted together as they are in free solution, with no cation being present.

Each solvated ion has different net charge and size. Thus, a sodium atom, being smaller than potassium can attract water molecules and bind them more closely to its nucleus than a potassium ion, which is larger. Thus, the size of a solvated ion/water complex (Ahydrated radius@) is larger for sodium than for potassium.

In a similar fashion, anions (negatively charged ions) have hydrated radii that can depend on the charge of the ion. Thus, a sulfonic acid residue which has three oxygen atoms bound to a sulfur atom, there are three locations where a partial negative charge can reside. Therefore, hydration shells can be formed around each of the oxygen atoms.

In addition to ionic and other charge-related effects, colloid osmotic effects can contribute to hydration of gels. Large molecular weight materials, such as proteins can form colloids in solution, and by vitrue of being solvated, contribute to colloid osmotic pressure, which can resist a tendency for the material to be compressed.

Thus, if water is bound tightly to the keratin, it is less likely to be forced away by hydrostatic pressure resulting from compression of the disc replacement by body weight. Conversely, if water is less tightly bound to the keratin or other material, water can be more easily expressed from the disc replacement and the disc material can become thinner.

In addition to charge/hydration effects, the total number of charges and the number of keratin molecules can affect the ability of a disc replacement to withstand compressive stress. Thus, increasing the amount of keratin, and/or increasing the sulfonation of the cysteic acid residues on the keratin can increase the ability of the keratin to retain a desirable shape within the intervertebral space.

In practice, one can measure the colloid osmotic pressure of keratin-based gels of this invention using standard methods known in the art. In general, it can be desirable for a keratin based gel to be able to remain hydrated at pressures corresponding to the load on the disc replacement while in use.

Figure 3:
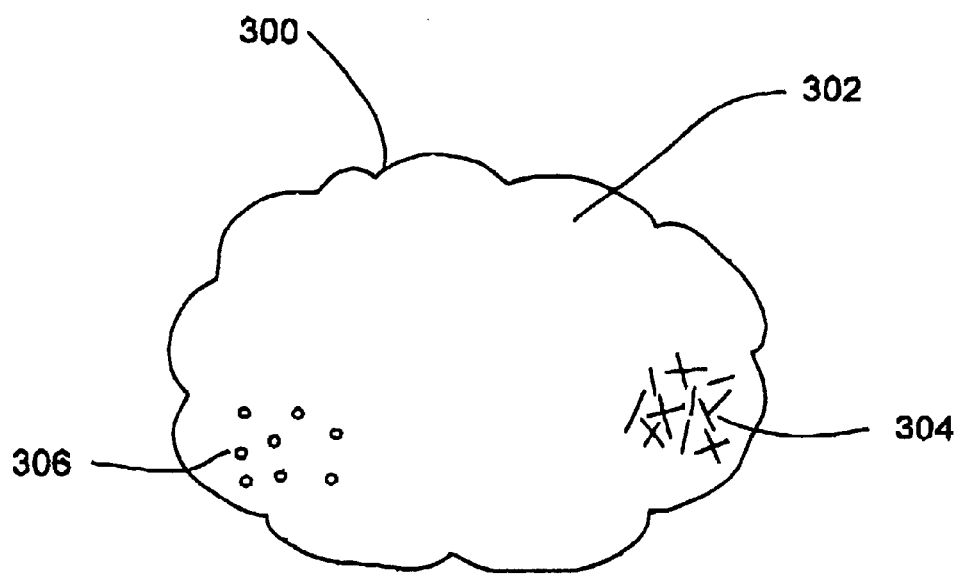
FIG. 3 depicts an embodiment of the invention using a keratin hydrogel which can be positioned in an intervertebral space.

FIG. 3 depicts an embodiment of this invention in which a non-encapsulated keratin hydrogel, which can be positioned within intervertebral spaces is deposited.

FIG. 3 depicts a keratin hydrogel 300 having relatively high polymer content and binds a relatively large amount of water. In this embodiment, the gel layer has a thickness that provides satisfactory separation of two adjacent vertebral bodies. Under load the gel becomes compressed by the extrusion of some water. However, sufficient water has been retained so that adjacent vertebral bodies do not impinge on one another. After the load is decreased, the gel can re-hydrate to maintain satisfactory separation of the adjacent vertebral bodies. Extrusion and re-hydration provide nutrients to cells and remove waste.

Example Embodiment of a Nucleus Pulposis Implant with No Envelope

The implant is comprised of a keratin-based hydrogel 302 placed in the space previously occupied by the degenerated nucleus pulposis. After the degenerated nucleus pulposis is removed, the hydrogel material may be delivered to the space via a syringe and needle, or a trephine and tamp or other methods used by those skilled in the art. Typically 0.5 to 6 cc of material will be needed to fill the evacuated space. The hydrogel material may be placed in the dehydrated, partially hydrated, or fully hydrated state. The hydrogel may be used as a carrier for growth factors 304 and/or cells 306. The compressive strength should be approximately 1 MPa, but preferably closer to 4 MPa. The hydrogel material should have equilibrium water content of between 75% to 90% by weight and a fixed charge density of approximately 0.28 meq/ml—both of which can be altered by the oxidation process. The oxidation and grinding process alters fixed charge density and surface area of the hydrogel material respectively. As the oxidation level is increased, the fixed charge density of the material increases. However, there is a threshold to the process, afterwhich, fixed charge density decreases. Also, as the material is ground to a finer powder, the surface area increases and more water can be bound. Again, there is a minimum threshold to particle size after which the material will no longer strongly bond to water.

The hydrogel is intended to restore the intervertebral disc height, place the annulus fibrosis in tension, and restore the diffusion/pumping mechanism used to supply nutrients to the intervertebral disc cells and remove waste products from the disc. If the hydrogel is seeded with cells, the restored pumping mechanism will provide nutrients to these cells and remove their waste products. If seeded with growth factors, the existing cells will proliferate and the nutrient supply will be maintained by the restored pumping mechanism. Likewise the waste products will be removed through the newly restored pumping mechanism.

Cells that may be added to the hydrogel may include fibrochondrocytes cultured from the annulus fibrosis or nucleus pulposis, chondrocytes, or fibroblasts. In addition, precursor mesenchymal stem cells may be added to the hydrogel. All cells are added to the hydrogel with the intent to promote matrix generation within the nucleus pulposis. Growth factors that may be added to the hydrogel include any factor from the TGF-beta family, VEGF, FGF, any keratin-based growth factor or any other factor that may induce cell differentiation, migration, and/or glycosaminoglycan production in the nuclear space. The growth factors will be added to the hydrogel with the intent of promoting nuclear matrix generation through induction, migration, and/or cellular production of matrix proteins.

2. Encapsulated Gels

In other embodiments of this invention, gels can be encapsulated to maintain their integrity under load-bearing conditions. Such encapsulation can be effected using polymer based materials, such as silicones, or can be keratin based, for example, using non-woven keratin material.

Suitable encapsulating polymers can include, byway of example only, polyethylene, poly(tetrafluoro)ethylene, polystyrene, polyester, silicone, and other synthetic polymers known in the art. Additionally, in some embodiments, it can be desirable to encapsulate a keratin hydrogel within a keratin capsule, such as a non-woven capsule. In certain embodiments, it can be desirable for the capsule to be non-porous, that is, to keep keratin, ions and water within the capsule. Alternatively, it can be desirable to provide a capsule having pores to permit the movement of water and/or small ions (e.g, sodium, chloride and the like) into and out of the capsule. Synthetic and non-synthetic polymers with pores of various sizes are known in the art. Pores can be made of a desired size sufficient to (1) keep water, ions and keratin within the capsule; (2) keep ions and keratin within the capsule; or (3) keep only keratin and/or other high molecular weight materials within the capsule.

1. Non-Porous Capsules and Envelope—Generally

In certain embodiments of this invention, it can be desirable to keep the water and ions within the capsule. For such embodiments, capsules having pores sufficiently small so that water molecules do not pass through. With these embodiments, the nucleus replacement may be able to withstand higher loads without substantial loss of thickness.

When a hydratable keratin is placed within such a capsule, water and ions can make contact with the keratin material. Upon hydration, the keratin material can swell to form a hydrogel. Thus, one role of the porous capsule is to keep the keratin materials positioned within the intravertebral space to provide support to the spine. As pressure on a nucleus replacement increases with increasing load, some of the water and/or ions might be extruded from the hydrogel, leave the capsule, and possibly leave the intravertebral space, thus, permitting a degree of compression of the capsule.

2. Water-Permeable Ion-Impermeable Capsules and Envelope—Generally

In other embodiments, it can be desirable for the sizes of the pores to be sufficiently small so that solvated ions are retained within the capsule, and for water to be able to leave. For these embodiments, the degree of compression of the nucleus replacement can be less than for embodiments in which ions can be extruded as well as water. By retaining ions within the capsule, more osmotically active particles can be retained within the capsule than in embodiments in which ions are extruded from the capsule.

Figure 4:
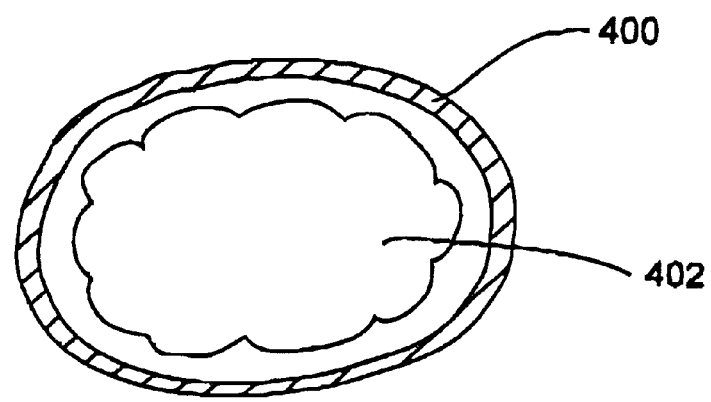
FIG. 4 depicts an embodiment of the invention wherein keratin hydrogel is encapsulated for positioning within an intervertebral space.

FIG. 4 depicts an embodiment of this invention in which keratin hydrogel 402 is encapsulated for positioning within an intervertebral space.

FIG. 4 depicts an embodiment in which the precursor or hydrogel encapsulating material 400 is non-porous. Under load, the disc replacement is not compressed.

Alternatively, the precursor or hydrogel encapsulating material 400 can be porous, and can have pores sized to permit the passage of water, but not ions or keratin polymers therethrough. In this embodiment, the load on the capsule is sufficient to extrude a small portion of the water, but the keratin material within the capsule retains sufficient water to keep the thickness of the nucleus replacement sufficient to maintain a desired separation of adjacent vertebral bodies.

3. Capsules Permeable to Water and Ions—Generally

FIG. 4 depicts an embodiment in which the precursor or hydrogel encapsulating material 400 is porous and has pores sized to permit the passage of water and solvated ions, but not large enough to permit passage of keratin materials. In this embodiment, the load on the capsule is sufficient to extrude some water and solvated ions, but the keratin material within the capsule retains sufficient water to keep the thickness of the disc sufficient to maintain a desired separation between adjacent vertebral bodies of a portion of the spine under flexion.

Such disc replacements can be useful in situations in which it is desirable for the dimensions of the nucleus replacement to be varied with the load. One example is in situations in which a degree of flexion is desired.

In yet other embodiments, the capsule can be made more or less flexible. By providing a relatively flexible capsule, the hydrogel within can move about in response to the subject's movements, without the capsule being damaged. In subjects having relatively mild damage, such flexible encapsulated keratin disc replacements can be especially useful to maximize spinal mobility.

Encapsulated keratin hydrogels can be made of differing sizes. In one series of embodiments, a capsule can be made sufficiently large to occupy substantially the entire area between vertebral bodies. Such "unitary" encapsulated gels can be especially useful for subjects in which the entire original disc must be replaced. It can be desirable for such unitary gels to have encapsulating material of sufficient strength to withstand the wall tension tending to pull the capsule material apart. It is known that for a cylinder, there is a relationship between the hydrostatic pressure, the radius of the cylinder and the wall tension necessary to keep the pressure within the cylinder contained. The relationship is known as LaPlace's law for a cylinder, and can be expressed by the following relationship:

$$\text{delta } P = \frac{T}{r},$$

where delta P is the pressure across the wall of a capsule ("transmural pressure"=pressure inside−pressure outside) of the cylinder, r is the radius and T is the wall tension. It can be appreciated that the ability of a material to withstand wall tension depends on the intrinsic strength of the material and the wall thickness. Thus, for materials having large intrinsic strength, the thickness of the wall can be less than for weaker materials.

Example Embodiment for a Nucleus Pulposis Implant—Single Envelope

The keratin-based hydrogel 402 described herein may be placed in an envelope 400 comprised of a keratin-based material or alternatively a suitably non-keratin based material. The envelope material may be in the form of a sheet material that may or may not include two external polyester layers and an inner keratin-based material. The sheet material may be processed in the form of a closed, continuous capsule. The envelope may be permeable or impermeable to cells, growth factors, and/or fluids. Permeability is based on the ability of the above mentioned items to freely pass through the envelope barrier. The hydrogel may be placed in the envelope prior to implantation in the nucleus cavity or after implantation. The hydrogel may be injected, poured, or tamped into the envelope. The hydrogel may be dehydrated, partially hydrated, or fully hydrated. The envelope may be sealed before or after the keratin hydrogel is placed.

The envelope may be impregnated with cells and/or growth factors and may be designed to bond to the vertebral endplates and/or annulus fibrosis. Cells that may be added to the hydrogel may include fibrochondrocytes cultured from the annulus fibrosis or nucleus pulposis, chondrocytes, or fibroblasts. In addition, precursor mesenchymal stem cells may be added to the hydrogel. All cells are added to the hydrogel with the intent to promote matrix generation within the nucleus pulposis. Growth factors that may be added to the hydrogel include any factor from the TGF-beta family, VEGF, FGF, any keratin-based growth factor or any other factor that may induce cell differentiation, migration, and/or glycosaminoglycan production in the nuclear space. Bonding between the envelope and host tissue may be in form of fibrous ingrowth. This fibrous ingrowth may involve fibrocartilage formation between the annulus fibrosis and/or cartilaginous endplates and the envelope. The newly generated fibrous tissue may form within the pores and/or on the surface of the envelope and span to the endplates and/or annulus tissue. Bonding may also be facilitated by using an adhesive. Such adhesives are known in the art.

The envelope may or may not be flexible or expandable and may or may not allow for changes in volume. Flexibility is defined as the ability of the material to change shape upon application of load, but not necessarily volume. Expandibility and compressibility are defined as the ability of the material to change volume upon load application. The changes in volume would be a direct result of the addition or subtraction of water from the hydrogel within the envelope. If the hydrogel imbibes fluid the volume will increase, and if fluid is released, the volume will decrease. The volume and dimensions of the envelope will be equal to or less than the volume of the evacuated nucleus pulposis space.

iv. Multi Chamber Embodiments

In other embodiments, it can be desirable to provide smaller encapsulated gels. For example, a group of relatively small gel capsules can be positioned within an intervertebral space. Each of such a group can provide some of the load-bearing functions. It can be readily appreciated that cylinders having the same wall tension and smaller radii can withstand greater transmural pressures than cylinders having larger radii. Thus, according to LaPlace's relationship, small capsules can withstand greater transmural pressures and loads than larger capsules. It can also be readily appreciated that even with relatively large capsules, one can provide greater load bearing capability by increasing the amounts of keratin, ions, and/or water within the capsule. If a portion of the load is borne by the keratin material within the capsule, less load need be borne by the capsule material.

Figure 5A:
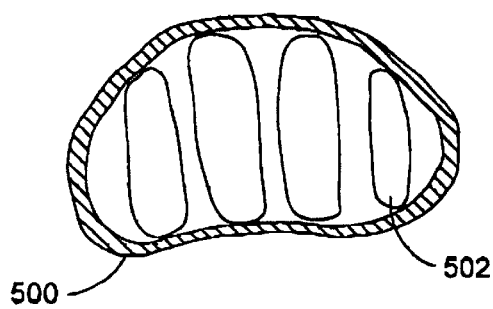
FIGS. 5a–5c depict embodiments of the invention including groups of capsules or envelopes for positioning within an intervertebral space.
Figure 5B:
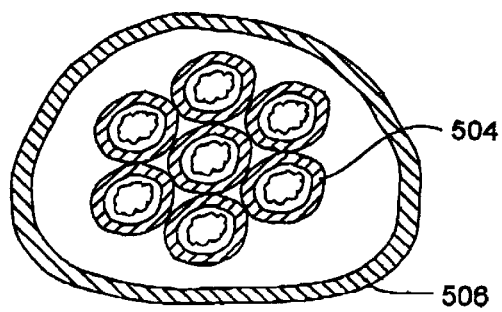
Figure 5C:
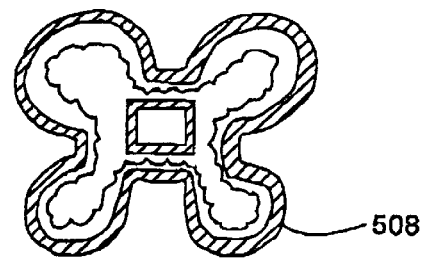

FIGS. 5*a*–5*c* depict embodiments of this invention in which groups of capsules are positioned within an intervertebral space.

FIG. 5*a* depicts an embodiment 500 in which 4 capsules 502 are provided for positioning within an intervertebral space of a subject having all the original disc replaced.

Nucleus Pulposis Implant—Individual Envelopes

The hydrogel described above will be placed in individual envelopes 504 and multiple envelopes will be placed in the evacuated nuclear space. The envelopes are similar those described earlier; they may be permeable or impermeable, they may be impregnated with growth factor and/or cells, and they may or may not conserve volume during deformation. Multiple individual envelopes may be placed in the intervertebral disc and may or may not be placed in one or more larger envelopes that contain(s) all of the smaller envelopes.

FIG. 5*b* depicts an embodiment 504 in which 7 capsules 506 are provided for positioning within an intervertebral space of a subject having a complete disc replacement. An outer wall 506 can be used as desired to encase the inner capsules.

Nucleus Pulposis Implant—Continuous, Multi-chambered Envelope

The envelope described above may be multi-chambered 508. The pathways connecting the multiple chambers may be designed to restrict the flow rate of the hydrogel from one chamber to another. In addition, the individual chambers may be positioned to direct the hydrogel from one anatomic area to another during motion.

In certain other embodiments, it can be desirable to provide a network of small capsules, connected together using tubes through which keratin hydrogel can move. FIG. 5*c* depicts an embodiment 508 of this invention in which several small capsules are in fluid communication with the other capsules in the group by way of connecting tubules. In such embodiments, increased load on one capsule can cause the hydrogel to flow throught the tubules to other capsules. Such a situation can occur during spinal flexion. For example, if a subject with such an embodiment bends forward, the load placed on ventral portions of adjacent vertebral processes increases. This then increases the load placed on those capsules near the ventral side of the vertebrae. The increased load causes hydrogel to be extruded into more dorsal capsules. It is to be understood that the embodiments of FIGS. 5*a*–5*c* can also be used on partial replacements of the disc.

Annulus Replacements—Generally

In certain subjects, the nucleus may be intact and relatively healthy, but the annulus may have suffered injury or disease, weakening the annulus to a point at which it may not support the nucleus sufficiently to prevent herniation, extrusion or destruction. In these subjects, it can be desirable to replace a portion of the annulus with an exogenous material.

Non-woven keratin materials can be provided that have sufficient strength to resist stretching and thereby can be used to augment or replace damaged annular materials. The strength necessary to prevent stretching can be approximated by LaPlace's law for cylinders, described herein above. Because the lateral load withstood by the annulus can be affected by the radius, the thickness of the material and the intrinsic strength of the annulus replacement can be selected so that the total wall tension during use does not exceed the strength of the annulus replacement.

In one series of embodiments, non-woven keratin material can be used as a single layer sheet. In other embodiments, multiple layers of keratin material can be used. In other embodiments, annular replacements can comprise multilayered structures having layers of keratin and other polymers, such as polyester, polypropylene, silicone, and others known in the art as described above for nucleus replacements. Moreover, in yet other embodiments, an annulus replacement can comprise co-precipitated polymers, wherein keratin and another type of polymer is formed in fashions as described above.

As with nucleus replacements, in certain embodiments, it can be desirable to include adjuncts in an annulus replacement. Such adjuncts include NSAIDS, cytokines, growth factors, or other molecules described herein or as known in the art Also, as with nucleus replacements, it may be desirable to include cells in an annulus replacement. Such cells can include osteoblasts, chondrocytes, fibroblasts or other cells whose presence can improve the healing or the post-surgical function of the annulus. In particular, fibroblasts can synthesize collagen, an extracellular fibrous protein that can strengthen the tissue. Osteoblasts can synthesize hydroxyapatite, a bone matrix material, and thereby strengthen the portion of an annulus replacement near bony tissues. Chondrocytes can synthesize chondroitin sulfate and other extracellular components of cartilage, and thereby provide in situ replacement of nucleus material and connective tissues.

In situations in which a partial annulus replacement or support is to be provided, it can be desirable to attach the annulus replacement to the remaining annulus, the vertebral bodies or to other tissues near the affected intervertebral space with sutures, adhesives, and other methods known to one of ordinary skill in the art. Such tissues include the bone, periosteum, ligaments, endplates and the remaining annulus. Such attachments can help localize the annulus replacement to those sites where it can have beneficial function. Also, such attachment can provide load bearing capability, if desired. For example, due to the wall tension applied on the annulus due to the LaPlace relationship previously described, attaching the annulus to the upper and lower vertebral bodies can help reduce the load between the existing, damaged annulus and the annulus replacement.

Example Embodiment for Annulus Fibrosis Repair—Sheet Material

Penetrations, defects, or damage to the annulus fibrosis may be repaired using a keratin-based material. The material may be placed at the damaged area to induce a repair response from the surrounding tissues and provide a scaffold for the repair response to take place. The material may be in the form of a sheet 600 that is placed on the inner and/or outer wall of the damaged annulus 602. The material 606 may be in the form of a plug 604 that is placed in the defect. The material 606 may also be securely anchored and tethered to the opposite inner annular wall 608. The purpose of each embodiment is to maintain its initial placement position during the repair process, repair the damaged annulus fibrosis and restore the pressure-vessel characteristics of the annulus. After the repair process takes place, the annulus should be able to provide restraint to the hydrostatic compression produced in the nucleus pulposis during loading, i.e. the annulus should act as a pressure vessel.

One aspect of the present invention is a nonwoven film composition comprising a synthetic polymer and a keratin material for use in annulus repair. The synthetic polymer may be, but is not limited to, α-olefins, acrylates, urethanes, acetates, nylon, esters, and copolymers thereof. An α-olefin is considered to be any monomer containing an α-double bond. The nonwoven composition may also further comprise a natural material which may be, but is not limited to, cotton. In some embodiments of the invention, the nonwoven composition is a laminate, which may be, but is not limited to, a tri-laminate comprising two outer layers of synthetic polymer and a middle layer of keratin material. The keratin material in the middle layer may be partially exposed by openings in the two outer nonwoven synthetic polymer layers. In some embodiments of the invention the synthetic polymer layers are nonwoven webs of polymer fibers. In other embodiments of the invention the synthetic polymer layers are nonwoven webs of polymer fibers.

Figure 6A:
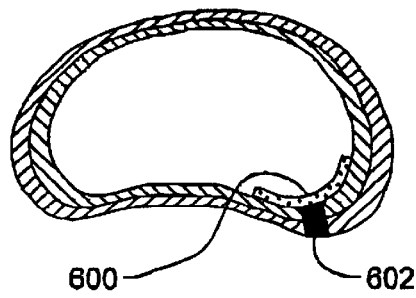
FIGS. 6a–6e depict embodiments of the invention relating to annulus and replacement.
Figure 6B:
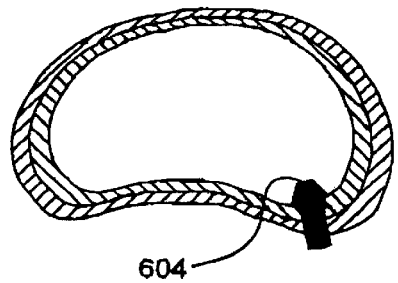
Figure 6C:
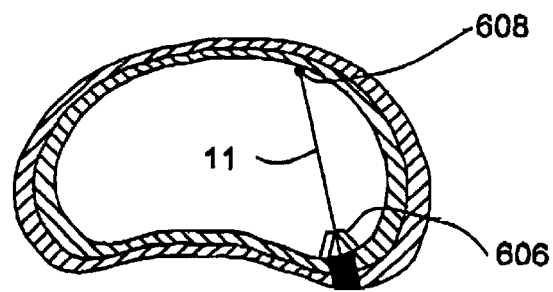
Figure 6D:
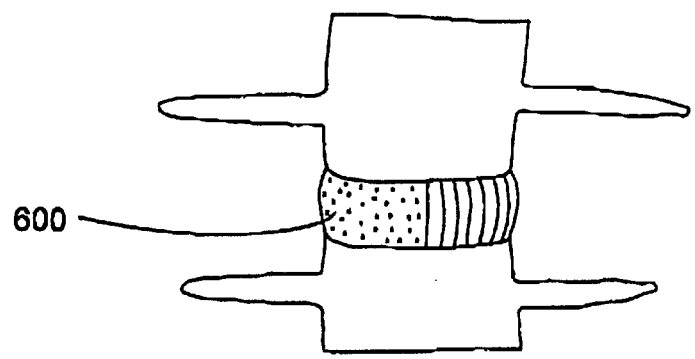
Figure 6E:
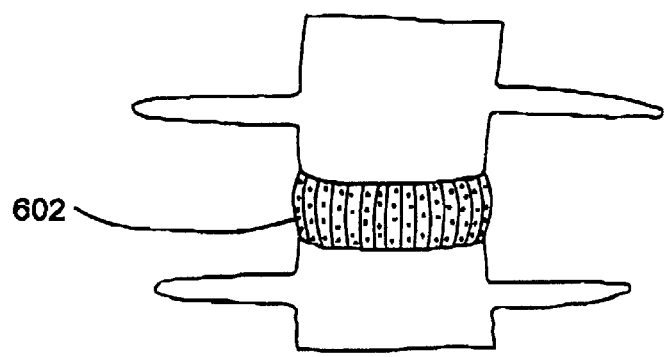

FIGS. 6d–6e also depict annulus replacements of this invention. FIG. 6d depicts a partial annulus replacement, wherein a portion of damaged original annulus is removed and replaced with a keratin based non-woven or woven sheet 600. FIG. 6e depicts a complete annulus replacement 600, wherein a sheet of keratin material is adhered to the upper and lower vertebral bodies using adhesive.

Annulus replacements can be premade having a variety of different sizes, thicknesses, compositions and physical properties. The surgeon can evaluate the needs of a particular patient and provide a properly sized annulus replacement during surgery.

What is claimed is:

1. An intervertebral disc implant comprising:
    a layer of keratin material which is adapted to be inserted between adjacent vertebral bodies, said keratin material comprising a keratin hydrogel wherein the keratin hydrogel is formed of keratin in which the cysteine amino acids are free of extrinsic chemical groups added by reduction of cystine disulfide bonds.
2. The intervertebral disc implant of claim 1 including: another layer of a polymer.
3. The intervertebral disc implant of claim 1 including: another layer of a synthetic polymer.
4. The intervertebral disc implant of claim 1 including: said layer be capsulated in one of the polyethylene, poly(tetrafluoro)ethylene, polystyrene, polyester, silicone, and other synthetic polymers.
5. The intervertebral disc implant of claim 1 including: the layer including keratin material deposited on a non-woven material.
6. The intervertebral disc implant of claim 1 including: the layer including keratin material deposited on a woven material.
7. The intervertebral disc implant of claim 1 including: the non-woven material being a polymer.
8. The intervertebral disc, implant of claim 1 including: the woven material being a polymer.
9. The intervertebral disc implant of claim 1 including: another layer of a keratin material.
10. The intervertebral disc implant of claim 1 including: a plurality of layers at least one of which is another layer of a keratin material and at least one is a layer of a polymer.

11. The intervertebral disc implant of claim 1 including:
   said layer of a keratin material sandwiched between layers of a polymer material.

12. The intervertebral disc implant of claim 1 including:
   said layer of keratin material shaped in a wedge shape in order to be adapted to fit between adjacent vertebral bodies.

13. The intervertebral disc implant of claim 1 including:
   said layer of keratin material being irregularly shaped in order to be adapted to fit between adjacent vertebral bodies.

14. The intervertebral disc implant of claim 1 including:
   said layer for partially replacing a nucleus of a vertebral disc.

15. The intervertebral disc implant of claim 1 including:
   said layer for replacing the entire nucleus of a vertebral disc.

16. The intervertebral disc implant of claim 1 including:
   said layer for at least partially replacing a nucleus and an annulus of a vertebral disc.

17. The intervertebral disc implant of claim 1 including:
   said layer including at least one of growth factors, and living cells.

18. The implant of claim 1 wherein said layer includes at least one of chondrocytes, fibrochondrocytes, fibroblasts, osteoblasts, and/or osteocytes.

19. The implant of claim 1 wherein said layer includes bone morphogenetic proteins (BMPs).

20. A method for repairing or replacing an intervertebral disc including the steps of:
   assessing the disc space of a patent;
   as necessary removing disc material of the patient;
   selecting an implant comprised of a keratin material, said keratin material comprising a keratin hydrogel wherein the keratin hydrogel is formed of keratin in which the cysteine amino acids are free of extrinsic chemical groups added by reduction of cystine disulfide bonds;
   placing the implant in the disc space; and closing.

* * * * *

UNITED STATES PATENT AND TRADEMARK OFFICE
CERTIFICATE OF CORRECTION

PATENT NO. : 6,783,546 B2
DATED : August 31, 2004
INVENTOR(S) : James F. Zucherman et al.

It is certified that error appears in the above-identified patent and that said Letters Patent is hereby corrected as shown below:

Column 28,
Line 12, delete "patent" please insert -- patient --.

Signed and Sealed this

Twenty-first Day of June, 2005

JON W. DUDAS
*Director of the United States Patent and Trademark Office*